US010806671B2

(12) United States Patent
Denenburg et al.

(10) Patent No.: US 10,806,671 B2
(45) Date of Patent: Oct. 20, 2020

(54) SYRINGE ASSEMBLY

(71) Applicant: West Pharma. Services IL, Ltd., Ra'anana (IL)

(72) Inventors: Igor Denenburg, Gedera (IL); Uri David, Nes Ziona (IL)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 0 days.

(21) Appl. No.: 16/326,993

(22) PCT Filed: Aug. 16, 2017

(86) PCT No.: PCT/IL2017/050903
§ 371 (c)(1),
(2) Date: Feb. 21, 2019

(87) PCT Pub. No.: WO2018/037398
PCT Pub. Date: Mar. 1, 2018

(65) Prior Publication Data
US 2019/0201290 A1  Jul. 4, 2019

(30) Foreign Application Priority Data
Aug. 21, 2016  (IL) ......................................... 247376

(51) Int. Cl.
*A61J 1/20* (2006.01)
*A61M 5/178* (2006.01)
(Continued)

(52) U.S. Cl.
CPC ........... *A61J 1/2096* (2013.01); *A61J 1/2031* (2015.05); *A61M 5/1782* (2013.01);
(Continued)

(58) Field of Classification Search
CPC ........ A61J 1/201; A61J 1/2031; A61J 1/2055; A61J 1/2096; A61M 5/1782; A61M 5/204;
(Continued)

(56) References Cited

U.S. PATENT DOCUMENTS

| 62,333 A | 2/1867 | Holl |
|---|---|---|
| 247,975 A | 10/1881 | Wickes |

(Continued)

FOREIGN PATENT DOCUMENTS

| CA | 2946559 A1 | 10/2015 |
|---|---|---|
| CN | 1636605 A | 7/2005 |

(Continued)

OTHER PUBLICATIONS

Int'l Search Report and Written Opinion dated Nov. 8, 2017 in Int'l Application No. PCT/IL2017/050903.
(Continued)

*Primary Examiner* — Benjamin J Klein
(74) *Attorney, Agent, or Firm* — Panitch Schwarze Belisario & Nadel LLP

(57) ABSTRACT

Syringe assemblies including a syringe pre-equipped with an integral liquid drug administration device for enabling administration of liquid drug contents and a drug vial adapter for telescopic mounting on a drug vial containing liquid drug contents. The drug vial adapter is initially mounted on the syringe and is intended to be manually detached therefrom to expose the integral liquid drug administration device. The syringe includes a flow control member having an initial flow path position for enabling filling the syringe with liquid drug contents from the drug vial and a final flow path position for enabling administration of liquid drug contents. Detachment of the drug vial adapter from the
(Continued)

syringe urges the flow control member from its initial flow path position to its final flow path position.

5 Claims, 12 Drawing Sheets

(51) Int. Cl.
    *A61M 5/20*     (2006.01)
    *A61M 5/32*     (2006.01)
    *A61M 39/22*     (2006.01)
    *A61M 5/31*     (2006.01)

(52) U.S. Cl.
    CPC .......... *A61M 5/204* (2013.01); *A61M 5/3202* (2013.01); *A61M 5/3297* (2013.01); *A61M 39/223* (2013.01); *A61J 1/201* (2015.05); *A61J 1/2055* (2015.05); *A61M 2005/3114* (2013.01); *A61M 2005/3118* (2013.01); *A61M 2005/3128* (2013.01); *A61M 2005/3201* (2013.01); *A61M 2209/045* (2013.01)

(58) Field of Classification Search
    CPC .............. A61M 5/3202; A61M 5/3297; A61M 2005/3114; A61M 2005/3118; A61M 2005/3128; A61M 39/223; A61M 2209/045
    See application file for complete search history.

(56) References Cited

U.S. PATENT DOCUMENTS

| | | | |
|---|---|---|---|
| 254,444 A | 2/1882 | Vogel |
| 300,060 A | 6/1884 | Ford |
| 1,021,681 A | 3/1912 | Jennings |
| 1,704,817 A | 3/1929 | Ayers |
| 1,930,944 A | 10/1933 | Schmitz, Jr. |
| 2,326,490 A | 8/1943 | Perelson |
| 2,560,162 A | 7/1951 | Garwood |
| 2,748,769 A | 6/1956 | Huber |
| 2,830,587 A | 4/1958 | Everett |
| 2,931,668 A | 4/1960 | Baley |
| 2,968,497 A | 1/1961 | Treleman |
| 3,059,643 A | 10/1962 | Barton |
| D198,499 S | 6/1964 | Harautuneian |
| 3,225,763 A | 12/1965 | Waterman |
| 3,277,893 A | 10/1966 | Clark |
| 3,308,822 A | 3/1967 | De Luca |
| 3,484,849 A | 12/1969 | Huebner et al. |
| 3,618,637 A | 11/1971 | Santomieri |
| 3,684,992 A | 8/1972 | Huguet et al. |
| 3,752,598 A | 8/1973 | Bowers et al. |
| 3,757,981 A | 9/1973 | Harris, Sr. et al. |
| 3,782,365 A | 1/1974 | Pinna |
| 3,788,524 A | 1/1974 | Davis et al. |
| 3,822,700 A | 7/1974 | Pennington |
| 3,826,261 A | 7/1974 | Killinger |
| 3,872,992 A | 3/1975 | Larson |
| 3,885,607 A | 5/1975 | Peltier |
| 3,938,520 A | 2/1976 | Scislowicz et al. |
| 3,957,052 A | 5/1976 | Topham |
| 3,977,555 A | 8/1976 | Larson |
| 3,993,063 A | 11/1976 | Larrabee |
| 4,020,839 A | 5/1977 | Klapp |
| 4,026,128 A | 5/1977 | Blanco |
| 4,051,852 A | 10/1977 | Villari |
| D247,975 S | 5/1978 | Luther |
| D248,568 S | 7/1978 | Ismach |
| 4,109,670 A | 8/1978 | Slagel |
| 4,121,585 A | 10/1978 | Becker, Jr. |
| 4,161,178 A | 7/1979 | Genese |
| 4,187,848 A | 2/1980 | Taylor |
| D254,444 S | 3/1980 | Levine |
| 4,203,067 A | 5/1980 | Fitzky et al. |
| 4,203,443 A | 5/1980 | Genese |
| 4,210,173 A | 7/1980 | Choksi et al. |
| D257,286 S | 10/1980 | Folkman |
| 4,253,501 A | 3/1981 | Ogle |
| 4,296,786 A | 10/1981 | Brignola |
| 4,303,067 A | 12/1981 | Connolly et al. |
| 4,312,349 A | 1/1982 | Cohen |
| 4,314,586 A | 2/1982 | Folkman |
| 4,328,802 A | 5/1982 | Curley et al. |
| 4,335,717 A | 6/1982 | Bujan et al. |
| D267,199 S | 12/1982 | Koenig |
| 4,376,634 A | 3/1983 | Prior et al. |
| D268,871 S | 5/1983 | Benham et al. |
| 4,392,850 A | 7/1983 | Elias |
| D270,282 S | 8/1983 | Gross |
| 4,410,321 A | 10/1983 | Pearson et al. |
| 4,411,662 A | 10/1983 | Pearson |
| D271,421 S | 11/1983 | Fetterman |
| 4,434,823 A | 3/1984 | Hudspith |
| 4,465,471 A | 8/1984 | Harris et al. |
| 4,475,915 A | 10/1984 | Sloane |
| 4,493,348 A | 1/1985 | Lemmons |
| 4,505,709 A | 3/1985 | Froning et al. |
| 4,507,113 A | 3/1985 | Dunlap |
| D280,018 S | 8/1985 | Scott |
| 4,532,969 A | 8/1985 | Kwaan |
| 4,564,054 A | 1/1986 | Gustavsson |
| 4,573,993 A | 3/1986 | Hoag et al. |
| 4,576,211 A | 3/1986 | Valentini et al. |
| 4,581,014 A | 4/1986 | Millerd et al. |
| 4,585,446 A | 4/1986 | Kempf |
| 4,588,396 A | 5/1986 | Stroebel et al. |
| 4,588,403 A | 5/1986 | Weiss et al. |
| D284,603 S | 7/1986 | Loignon |
| 4,604,093 A | 8/1986 | Brown et al. |
| 4,607,671 A | 8/1986 | Aalto et al. |
| 4,614,437 A | 9/1986 | Buehler |
| 4,638,975 A | 1/1987 | Iuchi et al. |
| 4,639,019 A | 1/1987 | Mittleman |
| 4,667,927 A | 5/1987 | Oscarsson |
| 4,675,020 A | 6/1987 | McPhee |
| 4,676,530 A | 6/1987 | Nordgren et al. |
| 4,683,975 A | 8/1987 | Booth et al. |
| 4,697,622 A | 10/1987 | Swift et al. |
| 4,721,133 A | 1/1988 | Sundblom |
| 4,729,401 A | 3/1988 | Raines |
| 4,735,608 A | 4/1988 | Sardam |
| 4,743,229 A | 5/1988 | Chu |
| 4,743,243 A | 5/1988 | Vaillancourt |
| 4,752,292 A | 6/1988 | Lopez et al. |
| 4,758,235 A | 7/1988 | Tu |
| 4,759,756 A | 7/1988 | Forman et al. |
| 4,778,447 A | 10/1988 | Velde et al. |
| 4,787,898 A | 11/1988 | Raines |
| 4,797,898 A | 1/1989 | Martinez |
| D300,060 S | 2/1989 | Molgaard-Nielsen |
| 4,804,366 A | 2/1989 | Zdeb et al. |
| 4,826,492 A | 5/1989 | Magasi |
| 4,832,690 A | 5/1989 | Kuu |
| 4,834,152 A | 5/1989 | Howson et al. |
| D303,013 S | 8/1989 | Konopka |
| 4,857,062 A | 8/1989 | Russell |
| 4,865,592 A | 9/1989 | Rycroft |
| 4,871,463 A | 10/1989 | Taylor et al. |
| 4,898,209 A | 2/1990 | Zbed |
| 4,909,290 A | 3/1990 | Coccia |
| 4,919,596 A | 4/1990 | Slate et al. |
| 4,927,423 A | 5/1990 | Malmborg |
| 4,931,040 A | 6/1990 | Haber et al. |
| 4,932,944 A | 6/1990 | Jagger et al. |
| 4,967,797 A | 11/1990 | Manska |
| D314,050 S | 1/1991 | Sone |
| D314,622 S | 2/1991 | Andersson et al. |
| 4,997,430 A | 3/1991 | Van der Heiden et al. |
| 5,006,114 A | 4/1991 | Rogers et al. |
| 5,035,686 A | 7/1991 | Crittenden et al. |
| 5,041,105 A | 8/1991 | D'Alo et al. |
| 5,045,066 A | 9/1991 | Scheuble et al. |
| 5,049,129 A | 9/1991 | Zdeb et al. |

(56) References Cited

U.S. PATENT DOCUMENTS

| | | |
|---|---|---|
| 5,053,015 A | 10/1991 | Gross |
| 5,061,248 A | 10/1991 | Sacco |
| 5,088,996 A | 2/1992 | Kopfer et al. |
| 5,096,575 A | 3/1992 | Cosack |
| 5,104,387 A | 4/1992 | Pokorney et al. |
| 5,113,904 A | 5/1992 | Aslanian |
| 5,122,124 A | 6/1992 | Novacek et al. |
| 5,125,908 A | 6/1992 | Cohen |
| 5,125,915 A | 6/1992 | Berry et al. |
| D328,788 S | 8/1992 | Sagae et al. |
| 5,171,230 A | 12/1992 | Eland et al. |
| 5,201,705 A | 4/1993 | Berglund et al. |
| 5,201,717 A | 4/1993 | Wyatt et al. |
| 5,203,771 A | 4/1993 | Melker et al. |
| 5,203,775 A | 4/1993 | Frank et al. |
| 5,211,638 A | 5/1993 | Dudar et al. |
| 5,232,029 A | 8/1993 | Knox et al. |
| 5,232,109 A | 8/1993 | Tirrell et al. |
| 5,242,432 A | 9/1993 | DeFrank |
| 5,247,972 A | 9/1993 | Tetreault |
| D341,420 S | 11/1993 | Conn |
| 5,269,768 A | 12/1993 | Cheung |
| 5,270,219 A | 12/1993 | DeCastro et al. |
| 5,279,576 A | 1/1994 | Loo et al. |
| 5,288,290 A | 2/1994 | Brody |
| 5,300,034 A | 4/1994 | Behnke et al. |
| 5,301,685 A | 4/1994 | Guirguis |
| 5,304,163 A | 4/1994 | Bonnici et al. |
| 5,304,165 A | 4/1994 | Haber et al. |
| 5,308,483 A | 5/1994 | Sklar et al. |
| 5,312,377 A | 5/1994 | Dalton |
| 5,328,474 A | 7/1994 | Raines |
| D349,648 S | 8/1994 | Tirrell et al. |
| 5,334,163 A | 8/1994 | Sinnett |
| 5,334,179 A | 8/1994 | Poll et al. |
| 5,342,346 A | 8/1994 | Honda et al. |
| 5,344,417 A | 9/1994 | Wadsworth, Jr. |
| 5,348,544 A | 9/1994 | Sweeney et al. |
| 5,348,548 A | 9/1994 | Meyer et al. |
| 5,350,372 A | 9/1994 | Ikeda et al. |
| 5,364,386 A | 11/1994 | Fukuoka et al. |
| 5,364,387 A | 11/1994 | Sweeney |
| 5,374,264 A | 12/1994 | Wadsworth, Jr. |
| 5,385,547 A | 1/1995 | Wong et al. |
| 5,397,303 A | 3/1995 | Sancoff et al. |
| D357,733 S | 4/1995 | Matkovich |
| 5,429,614 A | 7/1995 | Fowles et al. |
| 5,433,330 A | 7/1995 | Yatsko et al. |
| 5,445,630 A | 8/1995 | Richmond |
| 5,445,631 A | 8/1995 | Uchida |
| D362,718 S | 9/1995 | Deily et al. |
| 5,451,374 A | 9/1995 | Molina |
| 5,454,805 A | 10/1995 | Brony |
| 5,464,111 A | 11/1995 | Vacek et al. |
| 5,464,123 A | 11/1995 | Scarrow |
| 5,466,219 A | 11/1995 | Lynn et al. |
| 5,466,220 A | 11/1995 | Brenneman |
| 5,470,327 A | 11/1995 | Helgren et al. |
| 5,471,994 A | 12/1995 | Guirguis |
| 5,472,022 A | 12/1995 | Michel et al. |
| 5,478,337 A | 12/1995 | Okamoto et al. |
| 5,482,446 A | 1/1996 | Williamson et al. |
| 5,492,147 A | 2/1996 | Challender et al. |
| 5,496,274 A | 3/1996 | Graves et al. |
| D369,406 S | 4/1996 | Niedospial et al. |
| 5,505,714 A | 4/1996 | Dassa et al. |
| 5,509,433 A | 4/1996 | Paradis |
| 5,515,871 A | 5/1996 | Bittner et al. |
| 5,520,659 A | 5/1996 | Hedges |
| 5,526,853 A | 6/1996 | McPhee et al. |
| 5,527,306 A | 6/1996 | Raining |
| 5,531,695 A | 7/1996 | Swisher |
| 5,547,471 A | 8/1996 | Thompson et al. |
| 5,549,577 A | 8/1996 | Siegel et al. |
| 5,554,128 A | 9/1996 | Hedges |
| 5,562,686 A | 10/1996 | Sauer et al. |
| 5,562,696 A | 10/1996 | Nobles et al. |
| 5,566,729 A | 10/1996 | Grabenkort et al. |
| 5,569,191 A | 10/1996 | Meyer |
| 5,573,281 A | 11/1996 | Keller |
| 5,578,015 A | 11/1996 | Robb |
| 5,583,052 A | 12/1996 | Portnoff et al. |
| 5,584,819 A | 12/1996 | Kopfer |
| 5,591,143 A | 1/1997 | Trombley, III et al. |
| 5,603,706 A | 2/1997 | Wyatt et al. |
| 5,607,439 A | 3/1997 | Yoon |
| 5,611,576 A | 3/1997 | Guala |
| 5,616,203 A | 4/1997 | Stevens |
| 5,636,660 A | 6/1997 | Pfleiderer et al. |
| 5,637,101 A | 6/1997 | Shillington |
| 5,641,010 A | 6/1997 | Maier |
| 5,645,538 A | 7/1997 | Richmond |
| 5,647,845 A | 7/1997 | Haber et al. |
| 5,651,776 A | 7/1997 | Appling et al. |
| 5,653,686 A | 8/1997 | Coulter et al. |
| 5,658,133 A | 8/1997 | Anderson et al. |
| 5,672,160 A | 9/1997 | Osterlind et al. |
| 5,674,195 A | 10/1997 | Truthan |
| 5,676,346 A | 10/1997 | Leinsing |
| 5,685,845 A | 11/1997 | Grimard |
| D388,172 S | 12/1997 | Cipes |
| 5,695,829 A | 12/1997 | Quincy, III et al. |
| 5,699,821 A | 12/1997 | Paradis |
| 5,702,019 A | 12/1997 | Grimard |
| 5,718,346 A | 2/1998 | Weiler |
| 5,728,087 A | 3/1998 | Niedospial, Jr. |
| D393,722 S | 4/1998 | Fangrow, Jr. et al. |
| 5,738,144 A | 4/1998 | Rogers |
| 5,743,312 A | 4/1998 | Pfeifer et al. |
| 5,746,733 A | 5/1998 | Capaccio et al. |
| 5,752,942 A | 5/1998 | Doyle et al. |
| 5,755,696 A | 5/1998 | Caizza |
| 5,766,211 A | 6/1998 | Wood et al. |
| 5,772,630 A | 6/1998 | Ljungquist |
| 5,772,652 A | 6/1998 | Zielinski |
| RE35,841 E | 7/1998 | Frank et al. |
| 5,776,116 A | 7/1998 | Lopez et al. |
| 5,782,872 A | 7/1998 | Muller |
| 5,806,831 A | 9/1998 | Paradis |
| 5,810,792 A | 9/1998 | Fangrow, Jr. et al. |
| 5,814,020 A | 9/1998 | Gross |
| D399,559 S | 10/1998 | Molina |
| 5,817,082 A | 10/1998 | Niedospial, Jr. et al. |
| 5,820,621 A | 10/1998 | Yale et al. |
| 5,827,262 A | 10/1998 | Neftel et al. |
| 5,832,971 A | 11/1998 | Yale et al. |
| 5,833,213 A | 11/1998 | Ryan |
| 5,834,744 A | 11/1998 | Risman |
| 5,839,715 A | 11/1998 | Leinsing |
| 5,853,406 A | 12/1998 | Masuda et al. |
| D405,522 S | 2/1999 | Hoenig et al. |
| 5,868,710 A | 2/1999 | Battiato et al. |
| 5,871,110 A | 2/1999 | Grimard et al. |
| 5,873,872 A | 2/1999 | Thibault et al. |
| 5,879,337 A | 3/1999 | Kuracina et al. |
| 5,879,345 A | 3/1999 | Aneas |
| 5,887,633 A | 3/1999 | Yale et al. |
| 5,890,610 A | 4/1999 | Jansen et al. |
| 5,891,129 A | 4/1999 | Daubert et al. |
| 5,893,397 A | 4/1999 | Peterson et al. |
| 5,897,526 A | 4/1999 | Vaillancourt |
| 5,899,468 A | 5/1999 | Apps et al. |
| 5,902,280 A | 5/1999 | Powles et al. |
| 5,902,298 A | 5/1999 | Niedospial, Jr. et al. |
| D410,740 S | 6/1999 | Molina |
| 5,911,710 A | 6/1999 | Barry et al. |
| 5,919,182 A | 7/1999 | Avallone |
| 5,921,419 A | 7/1999 | Niedospial, Jr. et al. |
| 5,924,584 A | 7/1999 | Hellstrom et al. |
| 5,925,029 A | 7/1999 | Jansen et al. |
| 5,935,112 A | 8/1999 | Stevens et al. |
| 5,941,848 A | 8/1999 | Nishimoto et al. |
| 5,941,850 A | 8/1999 | Shah et al. |
| 5,944,700 A | 8/1999 | Nguyen et al. |

(56) References Cited

U.S. PATENT DOCUMENTS

| | | |
|---|---|---|
| 5,954,104 A | 9/1999 | Daubert et al. |
| 5,968,022 A | 10/1999 | Saito |
| 5,971,181 A | 10/1999 | Niedospial, Jr. et al. |
| 5,971,965 A | 10/1999 | Mayer |
| 5,989,237 A | 11/1999 | Fowles et al. |
| 6,003,566 A | 12/1999 | Thibault et al. |
| 6,004,278 A | 12/1999 | Botich et al. |
| 6,019,750 A | 2/2000 | Fowles et al. |
| 6,022,339 A | 2/2000 | Fowles et al. |
| 6,036,171 A | 3/2000 | Weinheimer et al. |
| 6,039,093 A | 3/2000 | Mrotzek et al. |
| 6,039,302 A | 3/2000 | Cote, Sr. et al. |
| D422,357 S | 4/2000 | Niedospial, Jr. et al. |
| 6,063,068 A | 5/2000 | Fowles et al. |
| D427,308 S | 6/2000 | Zinger |
| D427,309 S | 6/2000 | Molina |
| 6,070,623 A | 6/2000 | Aneas |
| 6,071,270 A | 6/2000 | Fowles et al. |
| 6,080,132 A | 6/2000 | Cole et al. |
| D428,141 S | 7/2000 | Brotspies et al. |
| 6,086,762 A | 7/2000 | Guala |
| 6,089,541 A | 7/2000 | Weinheimer et al. |
| 6,090,091 A | 7/2000 | Fowles et al. |
| 6,090,093 A | 7/2000 | Thibault et al. |
| 6,092,692 A | 7/2000 | Riskin |
| D430,291 S | 8/2000 | Jansen et al. |
| 6,099,511 A | 8/2000 | Devos |
| 6,113,068 A | 9/2000 | Ryan |
| 6,113,583 A | 9/2000 | Fowles et al. |
| 6,117,114 A | 9/2000 | Paradis |
| D431,864 S | 10/2000 | Jansen |
| 6,139,534 A | 10/2000 | Niedospial, Jr. et al. |
| 6,142,446 A | 11/2000 | Leinsing |
| 6,146,362 A | 11/2000 | Turnbull et al. |
| 6,149,623 A | 11/2000 | Reynolds |
| 6,156,025 A | 12/2000 | Niedospial, Jr. et al. |
| 6,159,192 A | 12/2000 | Fowles et al. |
| 6,168,037 B1 | 1/2001 | Grimard |
| 6,171,287 B1 | 1/2001 | Lynn et al. |
| 6,171,293 B1 | 1/2001 | Rowley et al. |
| 6,173,852 B1 | 1/2001 | Browne |
| 6,173,868 B1 | 1/2001 | DeJonge |
| 6,174,304 B1 | 1/2001 | Weston |
| 6,179,822 B1 | 1/2001 | Niedospial, Jr. |
| 6,179,823 B1 | 1/2001 | Niedospial, Jr. |
| 6,186,997 B1 | 2/2001 | Gabbard et al. |
| 6,206,861 B1 | 3/2001 | Mayer |
| 6,221,041 B1 | 4/2001 | Russo |
| 6,221,054 B1 | 4/2001 | Martin et al. |
| 6,221,065 B1 | 4/2001 | Davis |
| 6,238,372 B1 | 5/2001 | Zinger et al. |
| 6,245,044 B1 | 6/2001 | Daw et al. |
| D445,501 S | 7/2001 | Niedospial, Jr. |
| D445,895 S | 7/2001 | Svendsen |
| 6,253,804 B1 | 7/2001 | Safabash |
| 6,258,078 B1 | 7/2001 | Thilly |
| 6,280,430 B1 | 8/2001 | Neftel et al. |
| 6,290,688 B1 | 9/2001 | Lopez et al. |
| 6,296,621 B1 | 10/2001 | Masuda et al. |
| 6,299,131 B1 | 10/2001 | Ryan |
| 6,343,629 B1 | 2/2002 | Wessman et al. |
| 6,348,044 B1 | 2/2002 | Coletti et al. |
| 6,358,236 B1 | 3/2002 | DeFoggi et al. |
| 6,364,866 B1 | 4/2002 | Furr et al. |
| 6,378,576 B2 | 4/2002 | Thibault et al. |
| 6,378,714 B1 | 4/2002 | Jansen et al. |
| 6,379,340 B1 | 4/2002 | Zinger et al. |
| D457,954 S | 5/2002 | Wallace et al. |
| 6,382,442 B1 | 5/2002 | Thibault et al. |
| 6,386,397 B2 | 5/2002 | Brotspies et al. |
| 6,408,897 B1 | 6/2002 | Laurent et al. |
| 6,409,708 B1 | 6/2002 | Wessman |
| 6,440,107 B1 | 8/2002 | Trombley, III et al. |
| 6,453,949 B1 | 9/2002 | Chau |
| 6,453,956 B2 | 9/2002 | Safabash |
| 6,474,375 B2 | 11/2002 | Spero et al. |
| 6,478,788 B1 | 11/2002 | Aneas |
| D468,015 S | 12/2002 | Horppu |
| 6,499,617 B1 | 12/2002 | Niedospial, Jr. et al. |
| 6,503,240 B1 | 1/2003 | Niedospial, Jr. et al. |
| 6,503,244 B2 | 1/2003 | Hayman |
| 6,520,932 B2 | 2/2003 | Taylor |
| 6,524,278 B1 | 2/2003 | Campbell et al. |
| 6,524,295 B2 | 2/2003 | Daubert et al. |
| D472,316 S | 3/2003 | Douglas et al. |
| 6,530,903 B2 | 3/2003 | Wang et al. |
| 6,537,263 B1 | 3/2003 | Aneas |
| D472,630 S | 4/2003 | Douglas et al. |
| 6,544,246 B1 | 4/2003 | Niedospial, Jr. |
| 6,551,299 B2 | 4/2003 | Miyoshi et al. |
| 6,558,365 B2 | 5/2003 | Zinger et al. |
| 6,571,837 B2 | 6/2003 | Jansen et al. |
| 6,572,591 B2 | 6/2003 | Mayer |
| 6,575,955 B2 | 6/2003 | Azzolini |
| 6,581,593 B1 | 6/2003 | Rubin et al. |
| 6,582,415 B1 | 6/2003 | Fowles et al. |
| D476,731 S | 7/2003 | Cise et al. |
| 6,591,876 B2 | 7/2003 | Safabash |
| 6,599,273 B1 | 7/2003 | Lopez |
| 6,601,721 B2 | 8/2003 | Jansen et al. |
| 6,626,309 B1 | 9/2003 | Jansen et al. |
| 6,632,201 B1 | 10/2003 | Mathias et al. |
| 6,638,244 B1 | 10/2003 | Reynolds |
| D482,121 S | 11/2003 | Harding et al. |
| D482,447 S | 11/2003 | Harding et al. |
| 6,651,956 B2 | 11/2003 | Miller |
| 6,652,509 B1 | 11/2003 | Helgren et al. |
| D483,487 S | 12/2003 | Harding et al. |
| D483,869 S | 12/2003 | Tran et al. |
| 6,656,433 B2 | 12/2003 | Sasso |
| 6,666,852 B2 | 12/2003 | Niedospial, Jr. |
| 6,681,810 B2 | 1/2004 | Weston |
| 6,681,946 B1 | 1/2004 | Jansen et al. |
| 6,682,509 B2 | 1/2004 | Lopez |
| 6,692,478 B1 | 2/2004 | Paradis |
| 6,692,829 B2 | 2/2004 | Stubler et al. |
| 6,699,229 B2 | 3/2004 | Zinger et al. |
| 6,706,022 B1 | 3/2004 | Leinsing et al. |
| 6,706,031 B2 | 3/2004 | Manera |
| 6,715,520 B2 | 4/2004 | Andreasson et al. |
| 6,729,370 B2 | 5/2004 | Norton et al. |
| 6,736,798 B2 | 5/2004 | Ohkubo et al. |
| 6,745,998 B2 | 6/2004 | Doyle |
| 6,746,438 B1 | 6/2004 | Amissolle |
| 6,752,180 B2 | 6/2004 | Delay |
| D495,416 S | 8/2004 | Dimeo et al. |
| D496,457 S | 9/2004 | Prais et al. |
| 6,802,490 B2 | 10/2004 | Leinsing et al. |
| 6,832,994 B2 | 12/2004 | Niedospial, Jr. et al. |
| 6,852,103 B2 | 2/2005 | Fowles et al. |
| 6,875,203 B1 | 4/2005 | Fowles et al. |
| 6,875,205 B2 | 4/2005 | Leinsing |
| 6,878,131 B2 | 4/2005 | Novacek et al. |
| 6,884,253 B1 | 4/2005 | McFarlane |
| 6,890,328 B2 | 5/2005 | Fowles et al. |
| D506,256 S | 6/2005 | Miyoshi et al. |
| 6,901,975 B2 | 6/2005 | Aramata et al. |
| 6,945,417 B2 | 9/2005 | Jansen et al. |
| 6,948,522 B2 | 9/2005 | Newbrough et al. |
| 6,949,086 B2 | 9/2005 | Ferguson et al. |
| 6,951,613 B2 | 10/2005 | Reif et al. |
| 6,957,745 B2 | 10/2005 | Thibault et al. |
| 6,960,164 B2 | 11/2005 | O'Heeron |
| 6,972,002 B2 | 12/2005 | Thorne |
| 6,979,318 B1 | 12/2005 | McDonald et al. |
| RE38,996 E | 2/2006 | Crawford et al. |
| 6,994,315 B2 | 2/2006 | Ryan et al. |
| 6,997,916 B2 | 2/2006 | Simas, Jr. et al. |
| 6,997,917 B2 | 2/2006 | Niedospial, Jr. et al. |
| 7,024,968 B2 | 4/2006 | Raudabough et al. |
| 7,070,589 B2 | 7/2006 | Lolachi et al. |
| 7,074,216 B2 | 7/2006 | Fowles et al. |
| 7,083,600 B2 | 8/2006 | Meloul |
| 7,086,431 B2 | 8/2006 | D'Antonio et al. |

(56) References Cited

U.S. PATENT DOCUMENTS

| | | |
|---|---|---|
| 7,097,637 B2 | 8/2006 | Triplett et al. |
| 7,100,890 B2 | 9/2006 | Cote, Sr. et al. |
| 7,140,401 B2 | 11/2006 | Wilcox et al. |
| 7,150,735 B2 | 12/2006 | Hickle |
| 7,192,423 B2 | 3/2007 | Wong |
| 7,195,623 B2 | 3/2007 | Burroughs et al. |
| 7,241,285 B1 | 7/2007 | Dikeman |
| 7,294,122 B2 | 11/2007 | Kubo et al. |
| 7,306,199 B2 | 12/2007 | Leinsing et al. |
| D561,348 S | 2/2008 | Zinger et al. |
| 7,326,188 B1 | 2/2008 | Russell et al. |
| 7,326,194 B2 | 2/2008 | Zinger et al. |
| 7,350,764 B2 | 4/2008 | Raybuck |
| 7,354,422 B2 | 4/2008 | Riesenberger et al. |
| 7,354,427 B2 | 4/2008 | Fangrow |
| 7,425,209 B2 | 9/2008 | Fowles et al. |
| 7,435,246 B2 | 10/2008 | Zihlmann |
| D580,558 S | 11/2008 | Shigesada et al. |
| 7,452,348 B2 | 11/2008 | Hasegawa |
| 7,470,257 B2 | 12/2008 | Norton et al. |
| 7,470,265 B2 | 12/2008 | Brugger et al. |
| 7,472,932 B2 | 1/2009 | Weber et al. |
| 7,488,297 B2 | 2/2009 | Flaherty |
| 7,491,197 B2 | 2/2009 | Jansen et al. |
| 7,497,848 B2 | 3/2009 | Leinsing et al. |
| 7,523,967 B2 | 4/2009 | Steppe |
| 7,530,546 B2 | 5/2009 | Ryan et al. |
| D595,420 S | 6/2009 | Suzuki et al. |
| D595,421 S | 6/2009 | Suzuki et al. |
| 7,540,863 B2 | 6/2009 | Haindl |
| 7,540,865 B2 | 6/2009 | Griffin et al. |
| 7,544,191 B2 | 6/2009 | Peluso et al. |
| D595,862 S | 7/2009 | Suzuki et al. |
| D595,863 S | 7/2009 | Suzuki et al. |
| 7,611,487 B2 | 11/2009 | Woehr et al. |
| 7,611,502 B2 | 11/2009 | Daly |
| 7,615,041 B2 | 11/2009 | Sullivan et al. |
| 7,628,779 B2 | 12/2009 | Aneas |
| 7,632,261 B2 | 12/2009 | Zinger et al. |
| D608,900 S | 1/2010 | Giraud et al. |
| 7,654,995 B2 | 2/2010 | Warren et al. |
| 7,670,326 B2 | 3/2010 | Shemesh |
| 7,695,445 B2 | 4/2010 | Yuki |
| 7,704,229 B2 | 4/2010 | Moberg et al. |
| D616,090 S | 5/2010 | Kawamura |
| 7,713,247 B2 | 5/2010 | Lopez |
| 7,717,886 B2 | 5/2010 | Lopez |
| 7,722,090 B2 | 5/2010 | Burton et al. |
| D616,984 S | 6/2010 | Gilboa |
| 7,731,678 B2 | 6/2010 | Tennican et al. |
| 7,743,799 B2 | 6/2010 | Mosler et al. |
| 7,744,581 B2 | 6/2010 | Wallen et al. |
| 7,757,901 B2 | 7/2010 | Welp |
| 7,758,082 B2 | 7/2010 | Weigel et al. |
| 7,758,560 B2 | 7/2010 | Connell et al. |
| 7,762,524 B2 | 7/2010 | Cawthon et al. |
| 7,766,304 B2 | 8/2010 | Phillips |
| 7,771,383 B2 | 8/2010 | Truitt |
| D624,641 S | 9/2010 | Boclet |
| 7,799,009 B2 | 9/2010 | Niedospial, Jr. et al. |
| 7,803,140 B2 | 9/2010 | Fangrow, Jr. |
| D627,216 S | 11/2010 | Fulginiti |
| D630,732 S | 1/2011 | Lev et al. |
| 7,862,537 B2 | 1/2011 | Zinger et al. |
| 7,867,215 B2 | 1/2011 | Akerlund et al. |
| 7,879,018 B2 | 2/2011 | Zinger et al. |
| 7,883,499 B2 | 2/2011 | Fangrow |
| 7,895,216 B2 | 2/2011 | Longshaw et al. |
| D634,007 S | 3/2011 | Zinger et al. |
| 7,900,659 B2 | 3/2011 | Whitley et al. |
| D637,713 S | 5/2011 | Nord et al. |
| 7,963,954 B2 | 6/2011 | Kavazov |
| D641,080 S | 7/2011 | Zinger et al. |
| 7,985,216 B2 | 7/2011 | Daily et al. |
| D644,104 S | 8/2011 | Maeda et al. |
| 3,007,461 A1 | 8/2011 | Huo et al. |
| 7,993,328 B2 | 8/2011 | Whitley |
| 3,021,325 A1 | 9/2011 | Zinger et al. |
| 8,012,132 B2 | 9/2011 | Lum et al. |
| 8,016,809 B2 | 9/2011 | Zinger et al. |
| 8,025,653 B2 | 9/2011 | Capitaine et al. |
| 8,025,683 B2 | 9/2011 | Morrison |
| 8,029,472 B2 | 10/2011 | Leinsing et al. |
| 8,038,123 B2 | 10/2011 | Ruschke et al. |
| 8,066,688 B2 | 11/2011 | Zinger et al. |
| 8,070,739 B2 | 12/2011 | Zinger et al. |
| 8,075,550 B2 | 12/2011 | Nord et al. |
| 8,096,525 B2 | 1/2012 | Ryan |
| 8,105,314 B2 | 1/2012 | Fangrow, Jr. |
| D654,166 S | 2/2012 | Lair |
| D655,017 S | 2/2012 | Mosler et al. |
| 8,122,923 B2 | 2/2012 | Kraus et al. |
| 8,123,736 B2 | 2/2012 | Kraushaar et al. |
| D655,071 S | 3/2012 | Davila |
| D657,461 S | 4/2012 | Schembre et al. |
| 8,152,779 B2 | 4/2012 | Cabiri |
| 8,157,784 B2 | 4/2012 | Rogers |
| 8,167,863 B2 | 5/2012 | Yow |
| 8,172,824 B2 | 5/2012 | Pfeifer et al. |
| 8,177,768 B2 | 5/2012 | Leinsing |
| 8,182,452 B2 | 5/2012 | Mansour et al. |
| 8,187,248 B2 | 5/2012 | Zihlmann |
| 8,196,614 B2 | 6/2012 | Kriheli |
| 8,197,459 B2 | 6/2012 | Jansen et al. |
| 8,211,069 B2 | 7/2012 | Fangrow, Jr. |
| 8,225,959 B2 | 7/2012 | Lambrecht |
| 8,241,268 B2 | 8/2012 | Whitley |
| 8,262,628 B2 | 9/2012 | Fangrow, Jr. |
| 8,262,641 B2 | 9/2012 | Vedrine et al. |
| 8,267,127 B2 | 9/2012 | Kriheli |
| D669,980 S | 10/2012 | Lev et al. |
| 8,287,513 B2 | 10/2012 | Ellstrom et al. |
| 8,328,784 B2 | 12/2012 | Jensen et al. |
| D673,673 S | 1/2013 | Wang |
| D674,084 S | 1/2013 | Linnenschmidt |
| D674,088 S | 1/2013 | Lev et al. |
| 8,348,898 B2 | 1/2013 | Cabiri |
| D681,230 S | 4/2013 | Mosier et al. |
| 8,454,573 B2 | 6/2013 | Wyatt et al. |
| 8,469,939 B2 | 6/2013 | Fangrow, Jr. |
| 8,475,404 B2 | 7/2013 | Foshee et al. |
| 8,480,645 B1 | 7/2013 | Choudhury et al. |
| 8,480,646 B2 | 7/2013 | Nord et al. |
| 8,506,548 B2 | 8/2013 | Okiyama |
| 8,511,352 B2 | 8/2013 | Kraus et al. |
| 8,512,309 B2 | 8/2013 | Shemesh et al. |
| D690,009 S | 9/2013 | Schembre et al. |
| D690,418 S | 9/2013 | Rosenquist |
| 8,523,837 B2 | 9/2013 | Wiggins et al. |
| 8,545,476 B2 | 10/2013 | Ariagno et al. |
| 8,551,067 B2 | 10/2013 | Zinger et al. |
| 8,556,879 B2 | 10/2013 | Okiyama |
| 8,562,582 B2 | 10/2013 | Tuckwell et al. |
| 8,608,723 B2 | 12/2013 | Lev et al. |
| 8,628,508 B2 | 1/2014 | Weitzel et al. |
| 8,636,689 B2 | 1/2014 | Halili, Jr. et al. |
| 8,684,994 B2 | 4/2014 | Lev et al. |
| D714,935 S | 10/2014 | Nishioka et al. |
| D717,406 S | 11/2014 | Stanley et al. |
| D717,948 S | 11/2014 | Strong et al. |
| D719,650 S | 12/2014 | Arinobe et al. |
| D720,067 S | 12/2014 | Rosenquist |
| D720,451 S | 12/2014 | Denenburg et al. |
| D720,452 S | 12/2014 | Jordan |
| 8,900,212 B2 | 12/2014 | Kubo |
| 8,905,994 B1 | 12/2014 | Lev |
| 8,915,882 B2 | 12/2014 | Cabiri |
| D720,850 S | 1/2015 | Hsia et al. |
| D732,660 S | 6/2015 | Ohashi |
| D732,664 S | 6/2015 | Woehr et al. |
| D733,291 S | 6/2015 | Wang |
| D733,292 S | 6/2015 | Rogers |
| D733,293 S | 6/2015 | Rogers |
| 9,072,827 B2 | 7/2015 | Cabiri |

(56) References Cited

U.S. PATENT DOCUMENTS

| | | |
|---|---|---|
| D738,494 S | 9/2015 | Kashmirian |
| D741,457 S | 10/2015 | Guest |
| 9,149,575 B2 | 10/2015 | Cabiri |
| D750,235 S | 2/2016 | Maurice |
| 9,254,242 B2 | 2/2016 | Mueller et al. |
| D757,933 S | 5/2016 | Lev et al. |
| 9,339,438 B2 | 5/2016 | Lev et al. |
| 9,393,365 B2 | 7/2016 | Cabiri |
| 9,414,991 B2 | 8/2016 | Sanders et al. |
| 9,486,391 B2 | 11/2016 | Shemesh |
| 9,492,610 B2 | 11/2016 | Cabiri |
| 9,511,190 B2 | 12/2016 | Cabiri |
| 9,522,234 B2 | 12/2016 | Cabiri |
| D794,183 S | 8/2017 | Lev et al. |
| 9,763,855 B2 | 9/2017 | Fangrow |
| 9,801,786 B2 | 10/2017 | Lev et al. |
| 10,206,854 B2 | 2/2019 | Wu et al. |
| 10,376,654 B2 | 8/2019 | Sanders et al. |
| 2001/0000347 A1 | 4/2001 | Hellstrom et al. |
| 2001/0025671 A1 | 10/2001 | Safabash |
| 2001/0029360 A1 | 10/2001 | Miyoshi et al. |
| 2001/0051793 A1 | 12/2001 | Weston |
| 2002/0017328 A1 | 2/2002 | Loo |
| 2002/0055711 A1 | 5/2002 | Lavi et al. |
| 2002/0065488 A1 | 5/2002 | Suzuki et al. |
| 2002/0066715 A1 | 6/2002 | Niedospial |
| 2002/0087118 A1 | 7/2002 | Reynolds et al. |
| 2002/0087141 A1 | 7/2002 | Zinger et al. |
| 2002/0087144 A1 | 7/2002 | Zinger et al. |
| 2002/0104584 A1 | 8/2002 | Spero et al. |
| 2002/0115980 A1 | 8/2002 | Niedospial et al. |
| 2002/0121496 A1 | 9/2002 | Thiebault et al. |
| 2002/0123736 A1 | 9/2002 | Fowles et al. |
| 2002/0127150 A1 | 9/2002 | Sasso |
| 2002/0128628 A1 | 9/2002 | Fathallah |
| 2002/0138045 A1 | 9/2002 | Moen |
| 2002/0173752 A1 | 11/2002 | Polzin |
| 2002/0193777 A1 | 12/2002 | Aneas |
| 2003/0028156 A1 | 2/2003 | Juliar |
| 2003/0036725 A1 | 2/2003 | Lavi et al. |
| 2003/0068354 A1 | 4/2003 | Reif et al. |
| 2003/0069550 A1 | 4/2003 | Sharp |
| 2003/0073971 A1 | 4/2003 | Saker |
| 2003/0100866 A1 | 5/2003 | Reynolds |
| 2003/0109846 A1 | 6/2003 | Zinger et al. |
| 2003/0120209 A1 | 6/2003 | Jensen et al. |
| 2003/0135159 A1 | 7/2003 | Daily et al. |
| 2003/0153895 A1 | 8/2003 | Leinsing |
| 2003/0187420 A1 | 10/2003 | Akerlund et al. |
| 2003/0191445 A1 | 10/2003 | Wallen et al. |
| 2003/0195479 A1 | 10/2003 | Kuracina et al. |
| 2003/0199827 A1 | 10/2003 | Thorne |
| 2003/0199846 A1 | 10/2003 | Fowles et al. |
| 2003/0199847 A1 | 10/2003 | Akerlund et al. |
| 2003/0205843 A1 | 11/2003 | Adams |
| 2003/0236543 A1 | 12/2003 | Brenneman et al. |
| 2004/0010207 A1 | 1/2004 | Flaherty et al. |
| 2004/0024354 A1 | 2/2004 | Reynolds |
| 2004/0039365 A1 | 2/2004 | Aramata et al. |
| 2004/0044327 A1 | 3/2004 | Hasegawa |
| 2004/0073189 A1 | 4/2004 | Wyatt et al. |
| 2004/0143218 A1 | 7/2004 | Das |
| 2004/0143226 A1 | 7/2004 | Marsden |
| 2004/0153047 A1 | 8/2004 | Blank et al. |
| 2004/0158172 A1 | 8/2004 | Hancock |
| 2004/0162540 A1 | 8/2004 | Walenciak et al. |
| 2004/0167472 A1 | 8/2004 | Howell et al. |
| 2004/0181192 A1 | 9/2004 | Cuppy |
| 2004/0186424 A1 | 9/2004 | Hjertman |
| 2004/0199139 A1 | 10/2004 | Fowles et al. |
| 2004/0204699 A1 | 10/2004 | Hanly et al. |
| 2004/0217315 A1 | 11/2004 | Doyle |
| 2004/0225274 A1 | 11/2004 | Jansen et al. |
| 2004/0236305 A1 | 11/2004 | Jansen et al. |
| 2004/0249341 A1 | 12/2004 | Newbrough et al. |
| 2004/0255952 A1 | 12/2004 | Carlsen et al. |
| 2005/0015070 A1 | 1/2005 | Delnevo et al. |
| 2005/0016626 A1 | 1/2005 | Wilcox et al. |
| 2005/0049553 A1 | 3/2005 | Triplett et al. |
| 2005/0055008 A1 | 3/2005 | Paradis et al. |
| 2005/0082828 A1 | 4/2005 | Wicks et al. |
| 2005/0124964 A1 | 6/2005 | Niedospial et al. |
| 2005/0137523 A1 | 6/2005 | Wyatt et al. |
| 2005/0137566 A1 | 6/2005 | Fowles et al. |
| 2005/0148994 A1 | 7/2005 | Leinsing |
| 2005/0159706 A1 | 7/2005 | Wilkinson et al. |
| 2005/0159724 A1 | 7/2005 | Enerson |
| 2005/0182383 A1 | 8/2005 | Wallen |
| 2005/0209554 A1 | 9/2005 | Landau |
| 2005/0261637 A1 | 11/2005 | Miller |
| 2005/0277896 A1 | 12/2005 | Messerli et al. |
| 2006/0030832 A1 | 2/2006 | Niedospial et al. |
| 2006/0079834 A1 | 4/2006 | Tennican et al. |
| 2006/0089594 A1 | 4/2006 | Landau |
| 2006/0089603 A1 | 4/2006 | Truitt et al. |
| 2006/0095015 A1 | 5/2006 | Hobbs et al. |
| 2006/0106360 A1 | 5/2006 | Wong |
| 2006/0135948 A1 | 6/2006 | Varma |
| 2006/0155257 A1 | 7/2006 | Reynolds |
| 2006/0161192 A1 | 7/2006 | Young |
| 2006/0173410 A1 | 8/2006 | Moberg et al. |
| 2006/0178646 A1 | 8/2006 | Harris et al. |
| 2006/0195029 A1 | 8/2006 | Shults et al. |
| 2006/0212004 A1 | 9/2006 | Atil |
| 2006/0253084 A1 | 11/2006 | Nordgren |
| 2006/0259004 A1 | 11/2006 | Connell et al. |
| 2007/0016381 A1 | 1/2007 | Kamath et al. |
| 2007/0024995 A1 | 2/2007 | Hayashi |
| 2007/0060904 A1 | 3/2007 | Vedrine et al. |
| 2007/0078428 A1 | 4/2007 | Reynolds et al. |
| 2007/0079894 A1 | 4/2007 | Kraus et al. |
| 2007/0083164 A1 | 4/2007 | Barrelle et al. |
| 2007/0088252 A1 | 4/2007 | Pestotnik et al. |
| 2007/0088293 A1 | 4/2007 | Fangrow |
| 2007/0088313 A1 | 4/2007 | Zinger et al. |
| 2007/0106218 A1 | 5/2007 | Yodfat et al. |
| 2007/0106244 A1 | 5/2007 | Mosler et al. |
| 2007/0112324 A1 | 5/2007 | Harnedi-Sangsari |
| 2007/0156112 A1 | 7/2007 | Walsh |
| 2007/0167904 A1 | 7/2007 | Zinger et al. |
| 2007/0167912 A1 | 7/2007 | Causey et al. |
| 2007/0191760 A1 | 8/2007 | Iguchi et al. |
| 2007/0191764 A1 | 8/2007 | Zihlmann |
| 2007/0191767 A1 | 8/2007 | Hennessy et al. |
| 2007/0203451 A1 | 8/2007 | Murakami et al. |
| 2007/0219483 A1 | 9/2007 | Kitani et al. |
| 2007/0244447 A1 | 10/2007 | Capitaine et al. |
| 2007/0244461 A1 | 10/2007 | Fangrow |
| 2007/0244462 A1 | 10/2007 | Fangrow |
| 2007/0244463 A1 | 10/2007 | Warren et al. |
| 2007/0249995 A1 | 10/2007 | Van Manen |
| 2007/0255202 A1 | 11/2007 | Kitani et al. |
| 2007/0265574 A1 | 11/2007 | Tennican et al. |
| 2007/0265581 A1 | 11/2007 | Funamura et al. |
| 2007/0270778 A9 | 11/2007 | Zinger et al. |
| 2007/0287953 A1 | 12/2007 | Ziv et al. |
| 2007/0299404 A1 | 12/2007 | Katoh et al. |
| 2008/0009789 A1 | 1/2008 | Zinger et al. |
| 2008/0009822 A1 | 1/2008 | Enerson |
| 2008/0015496 A1 | 1/2008 | Hamedi-Sangsari |
| 2008/0132851 A1 | 6/2008 | Shaw et al. |
| 2008/0135051 A1 | 6/2008 | Lee |
| 2008/0172024 A1 | 7/2008 | Yow |
| 2008/0188799 A1 | 8/2008 | Mueller-Beckhaus et al. |
| 2008/0195049 A1 | 8/2008 | Thalmann et al. |
| 2008/0208138 A1 | 8/2008 | Lim et al. |
| 2008/0215015 A1 | 9/2008 | Cindrich et al. |
| 2008/0249473 A1 | 10/2008 | Ruth et al. |
| 2008/0249479 A1 | 10/2008 | Zinger et al. |
| 2008/0249498 A1 | 10/2008 | Fangrow |
| 2008/0262465 A1 | 10/2008 | Zinger et al. |
| 2008/0269687 A1 | 10/2008 | Chong et al. |
| 2008/0275407 A1 | 11/2008 | Scheurer |
| 2008/0287905 A1 | 11/2008 | Hiejima et al. |

(56) References Cited

U.S. PATENT DOCUMENTS

| | | |
|---|---|---|
| 2008/0294100 A1 | 11/2008 | de Costa et al. |
| 2008/0306439 A1 | 12/2008 | Nelson et al. |
| 2008/0312634 A1 | 12/2008 | Helmerson et al. |
| 2009/0012492 A1 | 1/2009 | Zihlmann |
| 2009/0043253 A1 | 2/2009 | Podaima |
| 2009/0054834 A1 | 2/2009 | Zinger et al. |
| 2009/0054852 A1 | 2/2009 | Takano et al. |
| 2009/0062767 A1 | 3/2009 | Van Antwerp et al. |
| 2009/0076360 A1 | 3/2009 | Brister et al. |
| 2009/0082750 A1 | 3/2009 | Denenburg et al. |
| 2009/0139724 A1 | 6/2009 | Gray et al. |
| 2009/0143758 A1 | 6/2009 | Okiyama |
| 2009/0177177 A1 | 7/2009 | Zinger et al. |
| 2009/0177178 A1 | 7/2009 | Pedersen |
| 2009/0187140 A1 | 7/2009 | Racz |
| 2009/0216103 A1 | 8/2009 | Brister et al. |
| 2009/0216212 A1 | 8/2009 | Fangrow, Jr. |
| 2009/0267011 A1 | 10/2009 | Hatton |
| 2009/0299325 A1 | 12/2009 | Vedrine et al. |
| 2009/0318946 A1 | 12/2009 | Tamesada |
| 2009/0326506 A1 | 12/2009 | Hasegawa et al. |
| 2010/0010443 A1 | 1/2010 | Morgan et al. |
| 2010/0016811 A1 | 1/2010 | Smith |
| 2010/0022985 A1 | 1/2010 | Sullivan et al. |
| 2010/0030181 A1 | 2/2010 | Helle et al. |
| 2010/0036319 A1 | 2/2010 | Drake et al. |
| 2010/0076397 A1 | 3/2010 | Reed et al. |
| 2010/0087786 A1 | 4/2010 | Zinger et al. |
| 2010/0137827 A1 | 6/2010 | Warren et al. |
| 2010/0137831 A1 | 6/2010 | Tsals |
| 2010/0152658 A1 | 6/2010 | Hanson et al. |
| 2010/0160889 A1 | 6/2010 | Smith et al. |
| 2010/0162548 A1 | 7/2010 | Leidig |
| 2010/0168664 A1 | 7/2010 | Zinger et al. |
| 2010/0168712 A1 | 7/2010 | Tuckwell et al. |
| 2010/0179506 A1 | 7/2010 | Shemesh et al. |
| 2010/0198148 A1 | 8/2010 | Zinger et al. |
| 2010/0204670 A1 | 8/2010 | Kraushaar et al. |
| 2010/0228220 A1 | 9/2010 | Zinger et al. |
| 2010/0241088 A1 | 9/2010 | Ranalletta et al. |
| 2010/0274184 A1 | 10/2010 | Chun |
| 2010/0274202 A1 | 10/2010 | Hyde et al. |
| 2010/0286661 A1 | 11/2010 | Raday et al. |
| 2010/0312220 A1 | 12/2010 | Kalitzki |
| 2011/0004143 A1 | 1/2011 | Beiriger et al. |
| 2011/0004184 A1 | 1/2011 | Proksch et al. |
| 2011/0044850 A1 | 2/2011 | Solomon et al. |
| 2011/0054440 A1 | 3/2011 | Lewis |
| 2011/0087164 A1 | 4/2011 | Mosier et al. |
| 2011/0125056 A1 | 5/2011 | Merchant |
| 2011/0144584 A1 | 6/2011 | Wozencroft |
| 2011/0160655 A1 | 6/2011 | Hanson et al. |
| 2011/0160701 A1 | 6/2011 | Wyatt et al. |
| 2011/0172636 A1 | 7/2011 | Aasmul |
| 2011/0175347 A1 | 7/2011 | Okiyama |
| 2011/0218511 A1 | 9/2011 | Yokoyama |
| 2011/0224640 A1 | 9/2011 | Kuhn et al. |
| 2011/0230856 A1 | 9/2011 | Kyle et al. |
| 2011/0264037 A1 | 10/2011 | Foshee et al. |
| 2011/0264069 A1 | 10/2011 | Bochenko |
| 2011/0276007 A1 | 11/2011 | Denenburg |
| 2011/0319827 A1 | 12/2011 | Leinsing et al. |
| 2012/0022344 A1 | 1/2012 | Kube |
| 2012/0022469 A1 | 1/2012 | Alpert |
| 2012/0053555 A1 | 3/2012 | Ariagno et al. |
| 2012/0059332 A1 | 3/2012 | Woehr et al. |
| 2012/0059346 A1 | 3/2012 | Sheppard et al. |
| 2012/0067429 A1 | 3/2012 | Mosler et al. |
| 2012/0071819 A1 | 3/2012 | Bruggemann et al. |
| 2012/0078214 A1 | 3/2012 | Finke et al. |
| 2012/0123382 A1 | 5/2012 | Kubo |
| 2012/0184938 A1 | 7/2012 | Lev et al. |
| 2012/0215182 A1 | 8/2012 | Mansour et al. |
| 2012/0220977 A1 | 8/2012 | Yow |
| 2012/0220978 A1 | 8/2012 | Lev et al. |
| 2012/0265163 A1 | 10/2012 | Cheng et al. |
| 2012/0271229 A1 | 10/2012 | Lev et al. |
| 2012/0296307 A1 | 11/2012 | Holt et al. |
| 2012/0310203 A1 | 12/2012 | Khaled et al. |
| 2012/0323172 A1* | 12/2012 | Lev ............... A61J 1/2096 604/87 |
| 2012/0323187 A1 | 12/2012 | Iwase et al. |
| 2012/0323210 A1 | 12/2012 | Lev et al. |
| 2013/0046269 A1 | 2/2013 | Lev et al. |
| 2013/0053814 A1 | 2/2013 | Mueller-Beckhaus et al. |
| 2013/0096493 A1 | 4/2013 | Kubo et al. |
| 2013/0110049 A1 | 5/2013 | Cronenberg et al. |
| 2013/0144248 A1 | 6/2013 | Putter et al. |
| 2013/0199669 A1 | 8/2013 | Moy et al. |
| 2013/0226100 A1 | 8/2013 | Lev |
| 2013/0231630 A1 | 9/2013 | Kraus et al. |
| 2013/0237904 A1 | 9/2013 | Deneburg et al. |
| 2013/0253448 A1 | 9/2013 | Baron et al. |
| 2013/0289530 A1 | 10/2013 | Wyatt et al. |
| 2014/0020793 A1 | 1/2014 | Denenburg et al. |
| 2014/0096862 A1 | 4/2014 | Aneas |
| 2014/0150911 A1 | 6/2014 | Planner et al. |
| 2014/0194854 A1 | 7/2014 | Tsals |
| 2014/0221940 A1 | 8/2014 | Clauson et al. |
| 2014/0277052 A1 | 9/2014 | Haselby et al. |
| 2014/0352845 A1 | 12/2014 | Lev et al. |
| 2015/0082746 A1 | 3/2015 | Ivosevic et al. |
| 2015/0088078 A1 | 3/2015 | Lev et al. |
| 2015/0112297 A1 | 4/2015 | Lev et al. |
| 2015/0290390 A1 | 10/2015 | Ring et al. |
| 2015/0297839 A1 | 10/2015 | Sanders et al. |
| 2015/0305770 A1 | 10/2015 | Fill et al. |
| 2016/0088995 A1 | 3/2016 | Ueda et al. |
| 2016/0166824 A1 | 6/2016 | Lev et al. |
| 2016/0199569 A1 | 7/2016 | Yevmenenko et al. |
| 2016/0228644 A1 | 8/2016 | Cabiri |
| 2016/0287475 A1 | 10/2016 | Yevmenenko et al. |
| 2016/0367439 A1 | 12/2016 | Davis et al. |
| 2019/0133885 A1 | 5/2019 | Wu et al. |

FOREIGN PATENT DOCUMENTS

| | | |
|---|---|---|
| CN | 1747683 A | 3/2006 |
| CN | 1863566 A | 11/2006 |
| CN | 1950049 A | 4/2007 |
| CN | 101001661 A | 7/2007 |
| CN | 101687083 A | 3/2010 |
| DE | 1064693 B | 9/1959 |
| DE | 1913926 A1 | 9/1970 |
| DE | 4122476 A1 | 1/1993 |
| DE | 0637443 A1 | 2/1995 |
| DE | 1408498 A1 | 5/1995 |
| DE | 19504413 A1 | 8/1996 |
| DE | 202004012714 U1 | 11/2004 |
| DE | 102007046951 B3 | 2/2009 |
| DE | 202009011019 U1 | 12/2010 |
| EM | 000627237-0001 | 1/2007 |
| EM | 001680703-0002 | 3/2010 |
| EP | 0192661 A1 | 9/1986 |
| EP | 0195018 A1 | 9/1986 |
| EP | 0258913 A2 | 3/1988 |
| EP | 0416454 A2 | 3/1991 |
| EP | 0282545 B1 | 2/1992 |
| EP | 0518397 A1 | 12/1992 |
| EP | 0521460 A1 | 1/1993 |
| EP | 582038 A2 | 2/1994 |
| EP | 0598918 A1 | 6/1994 |
| EP | 0737467 A1 | 10/1996 |
| EP | 761562 A1 | 3/1997 |
| EP | 765652 A1 | 4/1997 |
| EP | 765853 A1 | 4/1997 |
| EP | 0806597 A1 | 11/1997 |
| EP | 0814866 A1 | 1/1998 |
| EP | 829248 A2 | 3/1998 |
| EP | 0856331 A2 | 8/1998 |
| EP | 882441 A2 | 12/1998 |
| EP | 0887085 A2 | 12/1998 |
| EP | 0887885 A2 | 12/1998 |
| EP | 897708 A2 | 2/1999 |

(56) References Cited

FOREIGN PATENT DOCUMENTS

| | | |
|---|---|---|
| EP | 0898951 A1 | 3/1999 |
| EP | 960616 A2 | 12/1999 |
| EP | 1008337 A1 | 6/2000 |
| EP | 1029526 A1 | 8/2000 |
| EP | 1034809 A1 | 9/2000 |
| EP | 1051988 A2 | 11/2000 |
| EP | 1323403 A1 | 7/2003 |
| EP | 1329210 A1 | 7/2003 |
| EP | 1396250 A1 | 3/2004 |
| EP | 1454609 A1 | 9/2004 |
| EP | 1454650 A1 | 9/2004 |
| EP | 1498097 A2 | 1/2005 |
| EP | 1872824 A1 | 1/2008 |
| EP | 1911432 A1 | 4/2008 |
| EP | 1919432 A1 | 5/2008 |
| EP | 1930038 A2 | 6/2008 |
| EP | 2090278 A1 | 8/2009 |
| EP | 2351548 A1 | 8/2011 |
| EP | 2351549 A1 | 8/2011 |
| EP | 2462913 A1 | 6/2012 |
| EP | 2512399 A1 | 10/2012 |
| FR | 2029242 A5 | 10/1970 |
| FR | 2856660 A1 | 12/2004 |
| FR | 2869795 A1 | 11/2005 |
| FR | 2931363 A1 | 11/2009 |
| GB | 1444210 A | 7/1976 |
| IL | 186290 | 1/2008 |
| JP | 03-062426 B | 9/1991 |
| JP | 06-050656 U | 7/1994 |
| JP | H08-000710 A | 1/1996 |
| JP | 09-104460 A | 4/1997 |
| JP | 09-104461 A | 4/1997 |
| JP | 10-118158 | 5/1998 |
| JP | 110-504736 A | 5/1998 |
| JP | H11503627 A | 3/1999 |
| JP | 11-319031 A | 11/1999 |
| JP | 2000-508934 A | 7/2000 |
| JP | 2000-237278 A | 9/2000 |
| JP | 2000262497 A | 9/2000 |
| JP | 2001-505083 A | 4/2001 |
| JP | 2002-035140 A | 2/2002 |
| JP | 2002-516160 A | 6/2002 |
| JP | 2002-355318 A | 12/2002 |
| JP | 2003-033441 A | 2/2003 |
| JP | 2003-102807 A | 4/2003 |
| JP | 2004-501721 A | 1/2004 |
| JP | 2004-097253 A | 4/2004 |
| JP | 2004-522541 A | 7/2004 |
| JP | 2005-270629 A | 10/2005 |
| JP | 200661421 A | 3/2006 |
| JP | 2008-220961 A | 9/2008 |
| JP | 4329954 B2 | 9/2009 |
| JP | 0426403 A1 | 3/2010 |
| JP | 2010063622 A | 3/2010 |
| JP | 2010-179128 A | 8/2010 |
| JP | 2012-205769 A | 10/2012 |
| JP | 2014000220 A | 1/2014 |
| WO | 8601712 A1 | 3/1986 |
| WO | 8605683 A1 | 10/1986 |
| WO | 9003536 A1 | 4/1990 |
| WO | 9403373 A1 | 2/1994 |
| WO | 9507066 A1 | 3/1995 |
| WO | 9513785 A1 | 5/1995 |
| WO | 9600053 A1 | 1/1996 |
| WO | 9609083 A1 | 3/1996 |
| WO | 9629113 A1 | 9/1996 |
| WO | 9736636 A1 | 10/1997 |
| WO | 9832411 A1 | 7/1998 |
| WO | 9837854 A1 | 9/1998 |
| WO | 9961093 A1 | 12/1999 |
| WO | 0128490 A1 | 4/2001 |
| WO | 0130425 A1 | 5/2001 |
| WO | 0132524 A1 | 5/2001 |
| WO | 0160311 A1 | 8/2001 |
| WO | 0191693 A2 | 12/2001 |
| WO | 0202165 A2 | 1/2002 |
| WO | 200209797 A1 | 2/2002 |
| WO | 0236191 A2 | 5/2002 |
| WO | 02089900 A1 | 11/2002 |
| WO | 03051423 A2 | 6/2003 |
| WO | 03070147 A2 | 8/2003 |
| WO | 03079956 A1 | 10/2003 |
| WO | 2004041148 A1 | 5/2004 |
| WO | 2004096113 A2 | 11/2004 |
| WO | 2005002492 A1 | 1/2005 |
| WO | 2005018703 A2 | 3/2005 |
| WO | 2005041846 A2 | 5/2005 |
| WO | 2005105014 | 11/2005 |
| WO | 2005105014 A2 | 11/2005 |
| WO | 2006099441 A2 | 9/2006 |
| WO | 2007015233 A1 | 2/2007 |
| WO | 2007017868 A1 | 2/2007 |
| WO | 2007052252 A1 | 5/2007 |
| WO | 2007/105221 A1 | 9/2007 |
| WO | 2007101772 A1 | 9/2007 |
| WO | 2008076459 A1 | 6/2008 |
| WO | 2008081424 A2 | 7/2008 |
| WO | 02066100 A2 | 8/2008 |
| WO | 2008126090 A1 | 10/2008 |
| WO | 2009026443 A2 | 2/2009 |
| WO | 2009029010 A1 | 3/2009 |
| WO | 2009038860 A2 | 3/2009 |
| WO | 2009040804 A2 | 4/2009 |
| WO | 2009087572 A1 | 7/2009 |
| WO | 2009093249 A1 | 7/2009 |
| WO | 2009112489 A1 | 9/2009 |
| WO | 2009146088 A1 | 12/2009 |
| WO | 2010061743 A1 | 6/2010 |
| WO | 2010078227 A1 | 7/2010 |
| WO | 2010117580 A1 | 10/2010 |
| WO | 2011/004360 A1 | 1/2011 |
| WO | 0189607 A2 | 1/2011 |
| WO | 2011039747 A1 | 4/2011 |
| WO | 2011058545 A1 | 5/2011 |
| WO | 2011058548 | 5/2011 |
| WO | 2011058548 A1 | 5/2011 |
| WO | 2011077434 A1 | 6/2011 |
| WO | 2011090955 A1 | 7/2011 |
| WO | 2011104711 A1 | 9/2011 |
| WO | 2011156373 A1 | 12/2011 |
| WO | 2012/004790 A2 | 1/2012 |
| WO | 2012004784 A1 | 1/2012 |
| WO | 2012063230 | 5/2012 |
| WO | 2012063230 A1 | 5/2012 |
| WO | 2012143921 A1 | 10/2012 |
| WO | 2012150587 A1 | 11/2012 |
| WO | 2013127813 A1 | 9/2013 |
| WO | 2013134246 A1 | 9/2013 |
| WO | 2013148435 A1 | 10/2013 |
| WO | 2013156944 A1 | 10/2013 |
| WO | 2013156994 A1 | 10/2013 |
| WO | 2014033706 A2 | 3/2014 |
| WO | 2014033710 A1 | 3/2014 |
| WO | 2014099395 A1 | 6/2014 |
| WO | 2014170888 A1 | 10/2014 |
| WO | 2014174278 | 10/2014 |
| WO | 2014174278 A1 | 10/2014 |
| WO | 2016023590 | 2/2016 |
| WO | 2016023590 A1 | 2/2016 |

OTHER PUBLICATIONS

Grifols Vial Adapter Product Literature, 2 pages, Jan. 2002. cited by other.
Novel Transfer, Mixing and Drug Delivery Systems, MOP Medimop Medical Projects Ltd. Catalog, 4 pages, Rev. 4, 2004. cited by other.
Smart Site.RTM. Alaris Medical Systems Product Brochure, 4 pages, Issue 1, Oct. 1999. cited by other.
MixJect, downloaded from webpage: http://www.westpharma.com/en/products/pages/Mixject.aspx, Download Date: Aug. 8, 2012, 1 page.

(56) References Cited

OTHER PUBLICATIONS

MixJet Product Information Sheet, downloaded from webpage: http://www.westpharma.com/SiteCollectionDocuments/Recon/mixject%20product%20sheet.pdf; 1 page.
The MixJet transfer system, as shown in the article, "Advanced Delivery Devices," Drug Delivery Technology Jul./Aug. 2007 vol. 7 No. 7 [on-line]. [Retrieved from Internet May 14, 2020 URL: <http://www.drugdeiverytech-online.com/drugdelivery/200707/?pg=28pg28>. (3 pages).
Silicone Rubber Overview Downloaded from webpage: http://www.knovel.com/web/portal/browse/display?_EXT_KNOVEL_DISPLAY_bookid=1023&VerticalID=0 on Feb. 9, 2011, Download Date: Sep. 2, 2011, Original Posting Date: 2010, 6 pages.
Kipp, "Plastic Material Data Sheets," retrieved from the internet: http://www.knovel.com/web/portal/browse/display?_EXT_KNOVEL_DISPLAY_bookid=1023&VerticalID=0, retrieved on Feb. 9, 2011.
Alaris Medical Systems Product Brochure, 4 pages, Issue 1, Oct. 11, 1999.
Smart Site Needle-Free Systems, Alaris Medical Systems Webpage, 4 pages, Feb. 2006.
Photographs of Alaris Medical Systems SmartSite.RTM. device, 5 pages, 2002.
Non-Vented Vial Access Pin with Ultrasite.RTM. Valve, B. Braun Medical, Inc. website and product description, 3 pages, Feb. 2006.
Drug Administration Systems product information sheets; http://www.westpharma.com/eu/en/products/Pages/Vial2Bag.aspx; pp. 1-3 (admitted prior art).
Article with picture of West Pharmaceutical Services' Vial2Bag Needleless System, [on-line]; ISIPS Newsletter, Oct. 26, 2007]; retrieved from Internet Feb. 16, 2010]; URL:<http://www.isips.org/reports/ISIPS_Newsletter_October_26_2007. html.> (7 pages. see pp. 5-6).
West, Vial2Bag DC system, Oct. 2, 2014, https://web.archive.org/web/20141002065133/http://www.westpharma.cornien/products/Pages/Reconstitutionsystems.aspx.
Vial2Bag DC, downloaded from webpage: https://www.youtube.com/watch?v=FEOkglxNBrs, Original posting date: Aug. 21, 2014, 1 page.
Vial-Mate Adapter Device, Baxter, May 2017, downloaded from web page:http://www.baxtermedicationdeliveryproducts.com/drug-delivery/vialmate.html, Download Date: Jul. 28, 2017, original posting late: unknown, 1page.
Summit International Medical Technologies Inc., Vial Direct to Bag Spike 2020.
Merchant "An engineered control device for needle free reconstitution and transfer of compounded sterile intravenous drug solutions for immediate use to assist in complying with United States Pharmacopeia Chapter <797> standard", Adv Care, 2 pages, 2018.

* cited by examiner

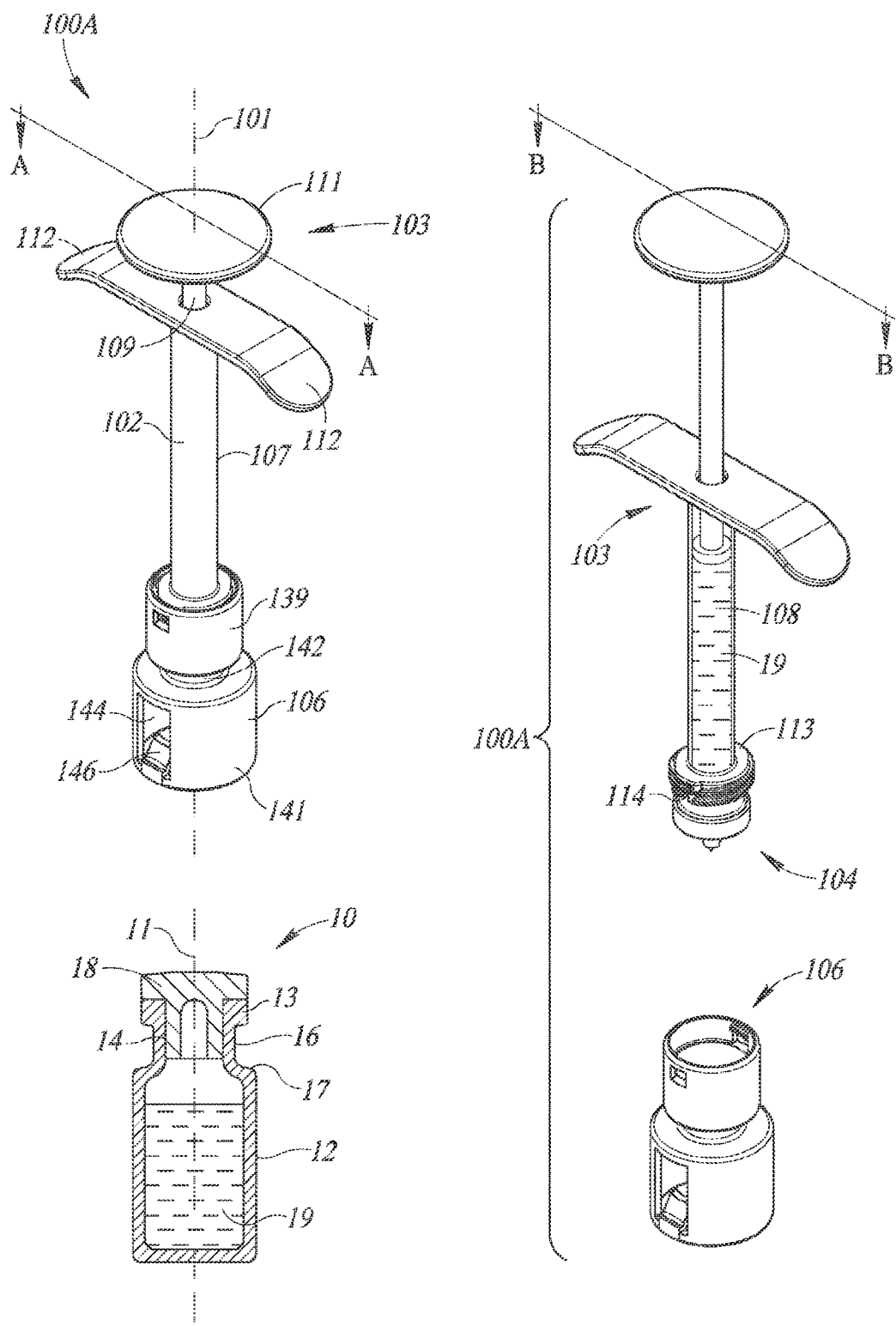

SYRINGE ASSEMBLY

CROSS-REFERENCE TO RELATED APPLICATIONS

This application is a Section 371 of International Application No. PCT/IL2017/050903, filed Aug. 16, 2017, which was published in the English language on Mar. 1, 2018 under International Publication No. WO 2018/037398 A1, which claims priority under 35 U.S.C. § 119 to Israeli Patent Application No. 247376, filed on Aug. 21, 2016, the disclosures of which are incorporated herein by reference.

FIELD OF THE INVENTION

The invention relates to syringe assemblies.

BACKGROUND OF THE INVENTION

Pre-filled syringes containing a liquid drug dosage ready for immediate administration can be equipped with either an integral standard intramuscular needle for intramuscular injection to a depth of about 1 cm or an integral intradermal micro-needle for intradermal injection to a depth of about 2-3 mm. Alternatively, pre-filled syringes can have a widened distal syringe tip preventing the attachment of a standard Luer connector needle hub and intended for oral administration of a liquid drug dosage. Pre-filled needle-equipped syringes have dead volumes considerably smaller than a standard Luer connector dead volume of about 0.03 ml to 0.05 ml which for certain vaccines is comparable to a vaccine dosage which can lead to considerable waste of vaccine.

Pre-filled syringes are filled with a liquid drug dosage as part of a manufacturing process for manufacturing same. Syringes with integral needles or a widened distal syringe tip can be filled with a liquid drug dosage by a clinical practitioner prior to use but such a manual filling process is generally regarded as time consuming and problematic. PCT International Application No. PCT/GB2014/051256 entitled Syringes and published under PCT International Publication No. WO 2014/174278 discloses a syringe assembly for assisting filling an initially empty syringe with a liquid drug dosage from a drug vial containing the liquid drug dosage.

There is a need for syringe assemblies including a syringe with an integral liquid drug administration device which can be readily filled with liquid drug contents immediately before use.

SUMMARY OF THE INVENTION

The present invention is directed toward syringe assemblies including a syringe pre-equipped with an integral liquid drug administration device and a drug vial adapter. The integral liquid drug administration device can be a standard intramuscular needle, a standard intradermal micro-needle, a widened distal syringe tip, and the like. The drug vial adapter is initially mounted on the syringe and intended to be manually detached therefrom to expose the integral liquid drug administration device for enabling administration of liquid drug contents. The syringe includes a flow control member having an initial flow path position for enabling manual filling the syringe with liquid drug contents from a drug vial and a final flow path position for enabling manual administration of liquid drug contents. Detachment of the drug vial adapter from the syringe urges the flow control member from its initial flow path position to its final flow path position. Detachment of the drug vial adapter from the syringe can be either by manual rotation or linear detachment of the drug vial adapter relative to the syringe.

The syringe assemblies of the present invention are preferably supplied with an empty syringe. A syringe assembly can be used with a drug vial containing liquid drug contents ready for immediate aspiration to an empty syringe. In the case of a drug vial containing powder medicament, a syringe assembly can preferably additionally include a liquid vial adapter for telescopic mounting on a liquid vial containing liquid contents for mixing with the powder medicament. The liquid contents can be diluent only for reconstitution or can include an active component. Such a syringe assembly employs its initial flow path position for three liquid transfers as follows: First liquid transfer for aspirating liquid contents from the liquid vial to the empty syringe. The liquid vial adapter and its empty liquid vial are necessarily detached from the syringe assembly after the first liquid transfer to enable telescopic mounting on a drug vial containing the power medicament. Second liquid transfer for injecting the liquid contents from the syringe into the drug vial to form the liquid drug contents. And third liquid transfer for aspirating the liquid drug contents from the drug vial into the empty syringe.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which:

FIG. 1 is a perspective view of a syringe assembly in an initial set-up position for use with a drug vial containing liquid drug contents;

FIG. 2 is a perspective view of the syringe assembly ready for administering liquid drug contents;

DETAILED DESCRIPTION OF PREFERRED EMBODIMENTS OF THE INVENTION

Figure 3:
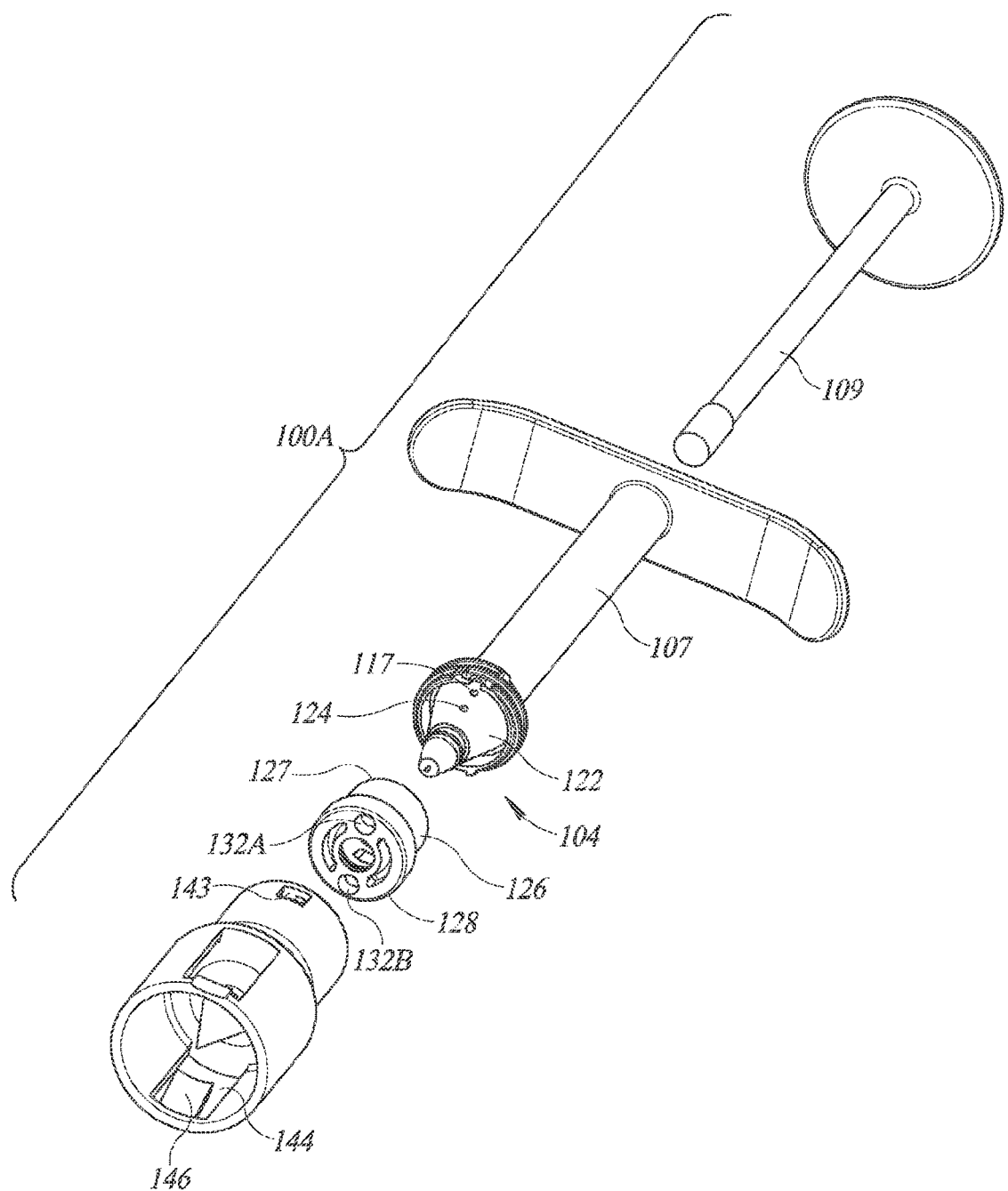
FIG. 3 is an exploded view of the syringe assembly.

FIG. 1 to FIG. 5 show a syringe assembly 100A for use with a drug vial 10. The drug vial 10 has a longitudinal drug vial centerline 11 and includes a drug vial tube 12, a tubular drug vial crown 13 having a drug vial crown opening 14 and a narrow diameter drug vial neck 16 intermediate the drug vial tube 12 and the drug vial crown 13. The drug vial 10 includes a drug vial shoulder 17 intermediate the drug vial tube 12 and the drug vial neck 16. The drug vial 10 includes a drug vial stopper 18 for stopping the drug vial crown opening 14. The drug vial 10 contains liquid drug contents 19. The drug vial 10 is either pre-filled with liquid drug contents or liquid drug contents are reconstituted therein prior to its use with the syringe assembly 100A.

The syringe assembly 100A has a longitudinal syringe assembly centerline 101 and includes a syringe 102 having a proximal syringe end 103 and a distal syringe tip 104, and a drug vial adapter 106. The syringe 102 includes an open-ended syringe barrel 107 having a proximal syringe barrel end 107A, a distal syringe barrel end 107B and a syringe barrel interior 108. The syringe 102 includes a plunger 109 with a thumb stop 111. The proximal syringe end 103 has a diametric pair of fingers grips 112. The distal syringe tip 104 is formed with an annular flange 113 transverse to the longitudinal syringe assembly centerline 101. The annular flange 113 is formed with an external screw thread 114. The distal syringe tip 104 is formed with a transverse directed lumen 116 extending between the distal syringe barrel end 107B and an aperture 117 formed distal to the annular flange 113 with respect to the proximal syringe end 103A.

The distal syringe tip 104 has a liquid drug dispensing lumen 119 co-axial with the longitudinal syringe assembly centerline 101. The liquid drug dispensing lumen 119 is fitted with an integral liquid drug administration device 121 constituted by a standard intradermal needle. The distal syringe tip 104 has a conical peripheral syringe tip surface 122 tapering from the distal syringe barrel end 107B towards the intradermal needle 121. The distal syringe tip 104 has a transverse directed lumen 123 spaced apart from the transverse directed lumen 116. The transverse directed lumen 123 extends between the liquid drug dispensing lumen 119 and an aperture 124 in the peripheral distal syringe tip surface 122. The two transverse directed lumens 116 and 123 lie on a longitudinal plane passing through the longitudinal syringe assembly centerline 101.

The syringe 102 includes a flow control member 126 having a tubular construction for snugly nesting between the distal syringe tip 104 and the drug vial adapter 106. The flow control member 126 has a proximal topside 127 and a distal underside 128. The flow control member 126 has a conical throughgoing bore 129 with an internal flow control member surface 131 in sealed contact with the peripheral distal syringe tip surface 122. The underside 128 is formed with a diametric pair of recesses 132A and 132B. The flow control member 126 has a diametric pair of flow channels for flow communication with the transverse directed lumen 116 for corresponding use in two flow path positions as follows: A longitudinal directed lumen 133 offset to the longitudinal syringe assembly centerline 101 for use in an initial flow path position. The lumen 133 extends between an aperture 134 formed in the internal flow control member surface 131 and the recess 132A. And a groove 136 formed in the internal flow control member surface 131 for flow communication between the two transverse directed lumens 116 and 123 in a final flow path position. The groove 136 has a proximal groove end 137 and a distal groove end 138. The aperture 134 and the proximal groove end 137 are diametric opposite on the same plane transverse to the longitudinal syringe assembly centerline 101.

The drug vial adapter 106 has a tubular construction and includes a proximal upright stem 139, a distal downward depending skirt 141 for telescopic mounting on the drug vial 10 and an intermediate neck 142 between the upright stem 139 and the downward depending skirt 141. The upright stem 139 has diametric pair of inward directed screw thread protrusions 143 for screw thread mounting on the external screw thread 114. The drug vial adapter 106 requires a half turn to detach from the distal syringe tip 104 and concurrently rotate the flow control member 126 from its initial flow path position to its final flow path position. The upright stem 139 and the intermediate neck 142 enclose the distal syringe tip 104 and the flow control member 126. The skirt 141 includes a diametric pair of longitudinal directed apertures 144 having inward directed protrusions 146 for snap fitting on the drug vial crown 13 and a puncturing cannula 147 with a puncturing cannula tip 147A for puncturing the drug vial stopper 18 on snap fitting on the drug vial 10. The neck 142 includes a diametric pair of protrusions 148A and 148B for corresponding snug insertion in the diametric pair of recesses 132A and 132B. The puncturing cannula 147 includes a lumen 149 extending between an aperture 151 in the protrusion 148A and an aperture 152 at the puncturing cannula tip 147A.

Figure 4:
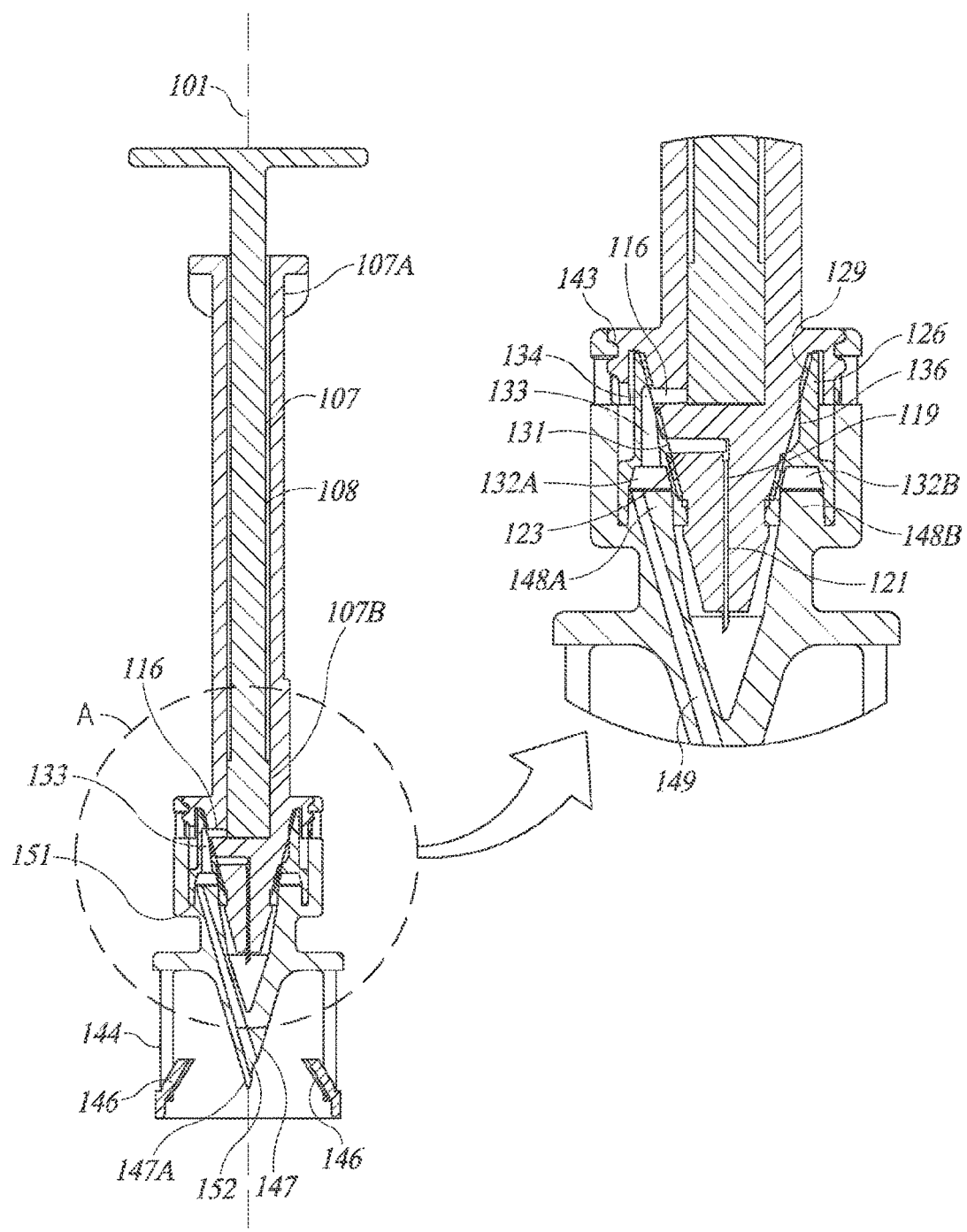
FIG. 4 is a longitudinal cross section of the syringe assembly along line A-A in FIG. 1 and an enlargement of encircled region A.
Figure 5:
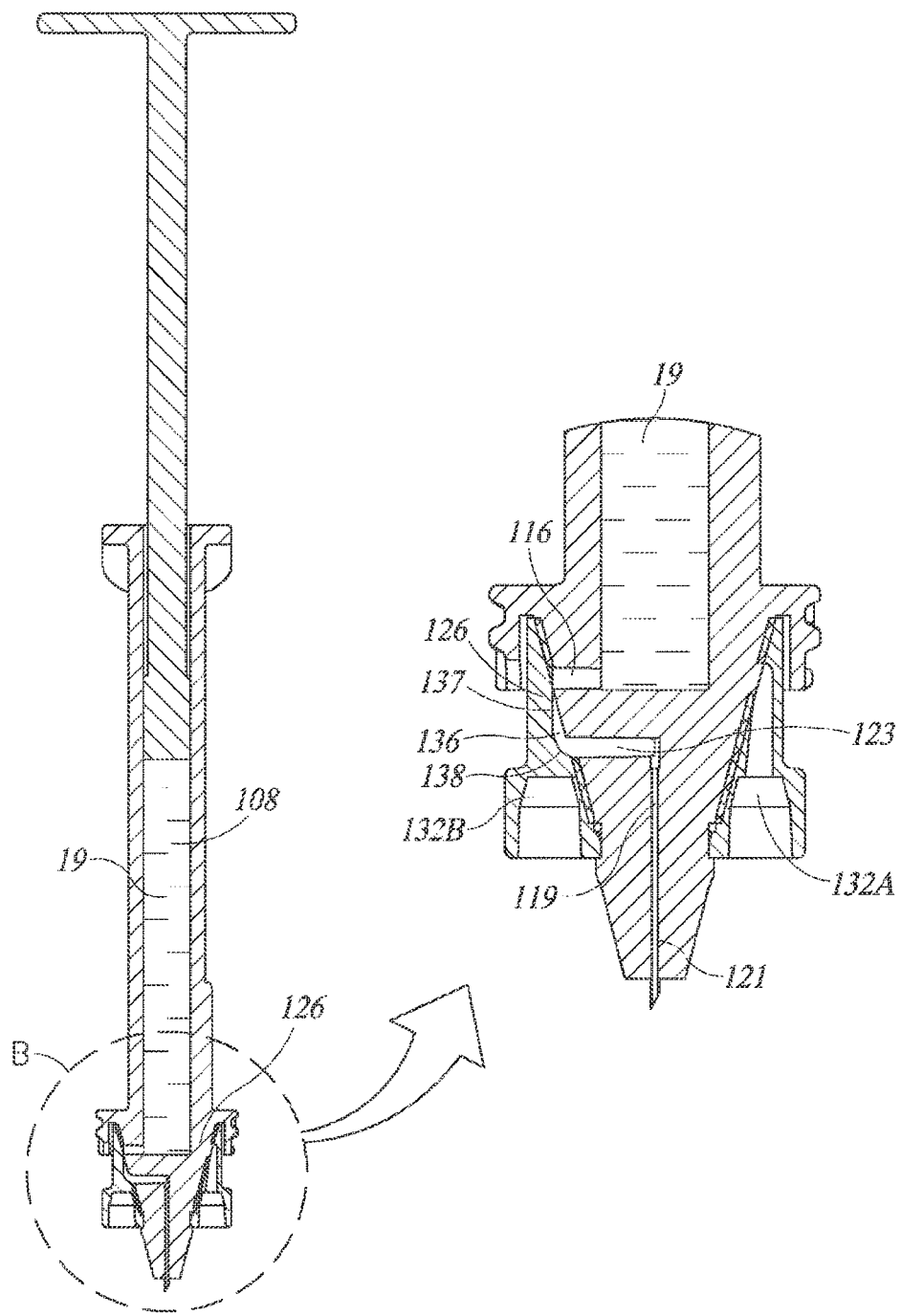
FIG. 5 is a longitudinal cross section of the syringe assembly along line B-B in FIG. 2 and an enlargement of encircled region B.

FIG. 4 shows the syringe assembly 100A has an initial flow path between the syringe barrel interior 108 and the puncturing cannula 147 via the lumen 116, the lumen 133 and the lumen 149. FIG. 5 shows the syringe assembly 100A has a final flow path between the syringe barrel interior 108 and the intradermal needle 121 via the lumen 116, the groove 136 and the liquid drug dispensing lumen 119.

Figure 6C:
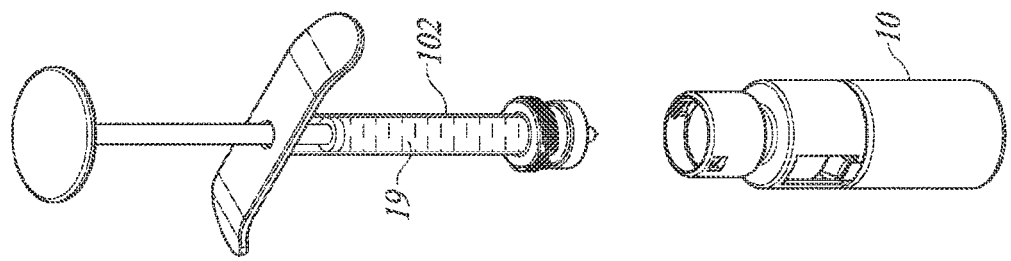
FIG. 6A to FIG. 6C show the use of the syringe assembly for administering liquid drug contents.
Figure 6B:
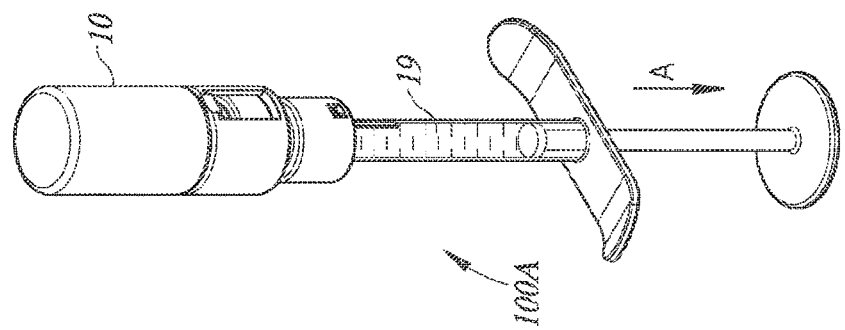
Figure 6A:
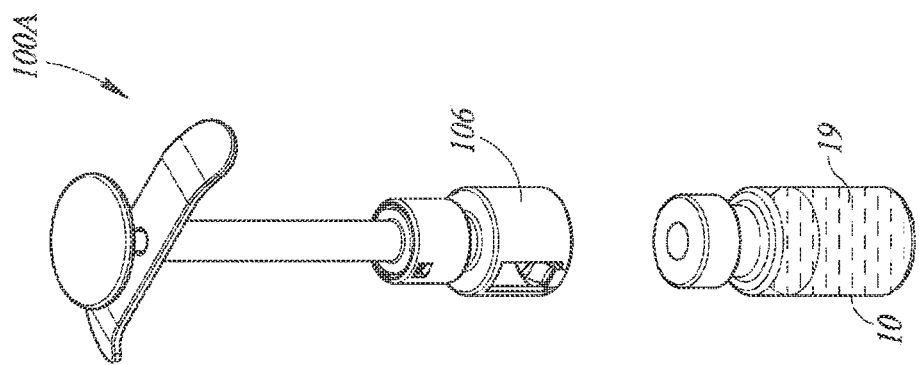

FIG. 6A to FIG. 6C show the use of the syringe assembly 100A as follows: FIG. 6A shows the syringe assembly 100A in an initial set-up position in which the drug vial adapter 106 is detachably mounted on the distal syringe tip 104. The plunger 109 is fully inserted position and the flow control member 126 is in its initial flow control position as show in FIG. 4. A clinical practitioner telescopically mounts the drug vial adapter 106 on a drug vial 10 for puncturing same. FIG. 6B shows the clinical practitioner inverts the syringe assembly 100A and the punctured drug vial 10 to aspirate the liquid drug contents 19 from the drug vial 10 into the syringe 102 as denoted by arrow A. FIG. 6C shows the clinical practitioner inverts the syringe assembly 100A and the now empty drug vial 10 to its upright position. The clinical practitioner rotates the drug vial adapter 106 through a half turn to detach it together with the empty drug vial 10 from the distal syringe tip 104 to expose the intradermal needle 121 and urge the flow control member 126 to its final flow path position. The syringe 102 is ready for administering the liquid drug contents 19.

Figure 7:
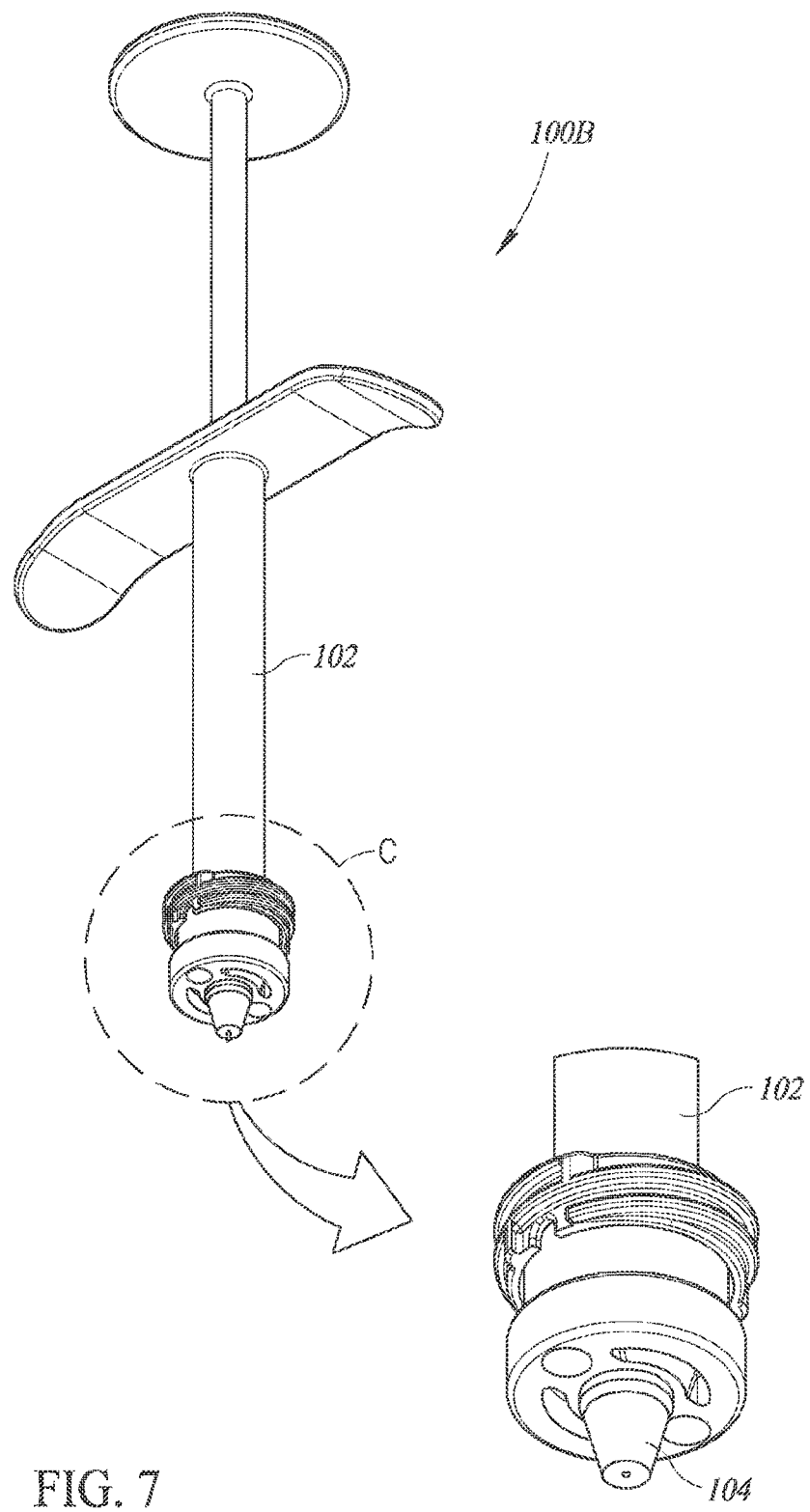
FIG. 7 is a perspective view of a syringe with a widened distal syringe tip for oral administration of liquid drug contents and an enlargement of encircled region C.
Figure 8:
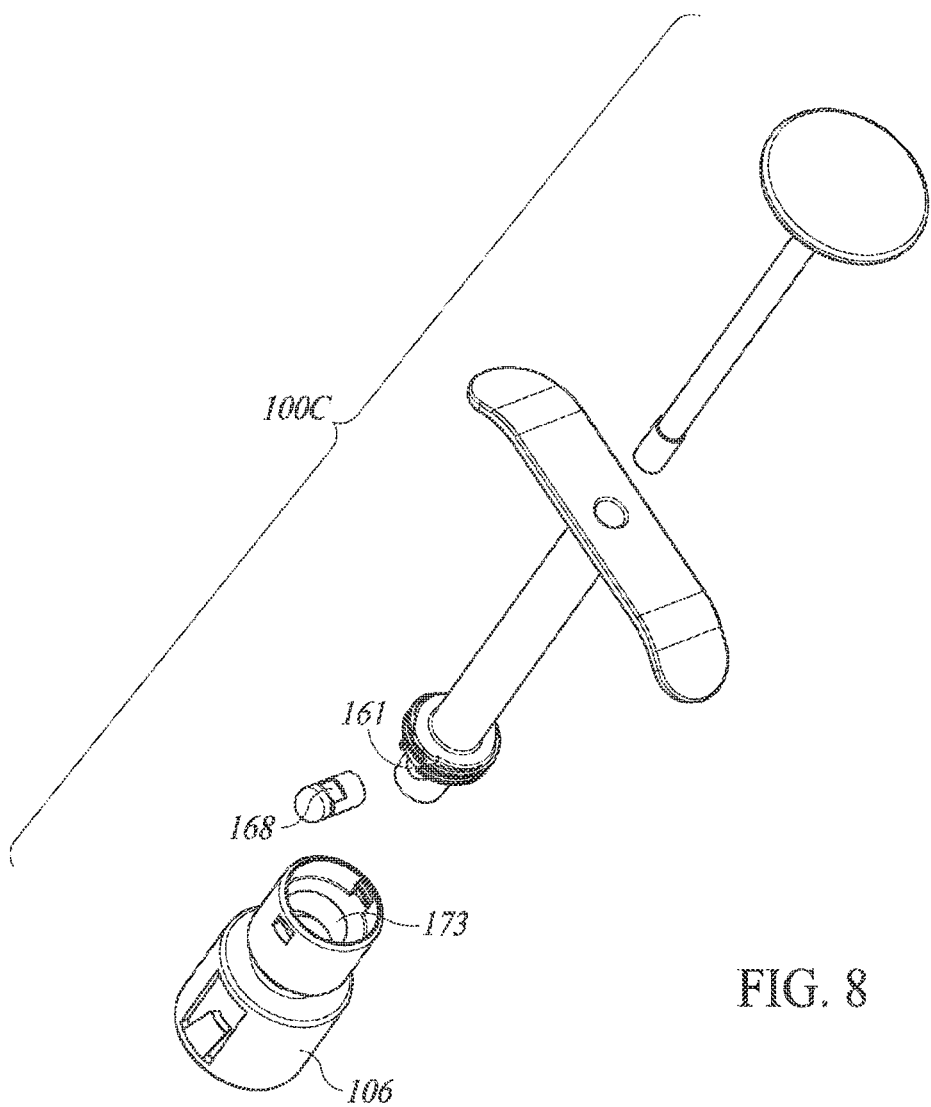
FIG. 8 is an exploded view of an alternative syringe assembly.
Figure 9:
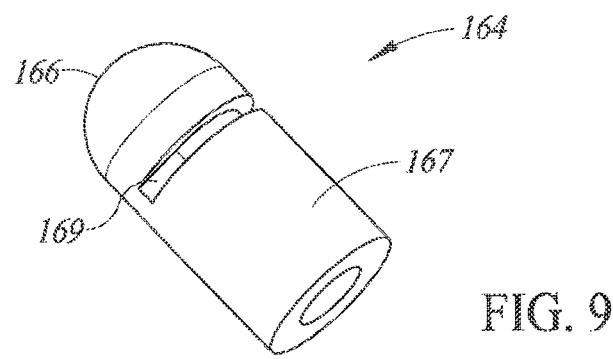
FIG. 9 is a rear perspective view of a flow control member of the FIG. 8 syringe assembly.

FIG. 7 shows a syringe assembly 100B including a syringe 102 having a widened distal syringe tip 104 constituting an integral liquid drug administration device for oral administration of liquid drug contents.

FIG. 8 to FIG. 11 show a syringe assembly 100C similar in construction and use as the syringe assembly 100A and therefore similar parts are likewise numbered. The latter 100C differs from the former 100A in terms of its flow control arrangement for aspirating liquid drug contents from a drug vial and administrating liquid drug contents.

The distal syringe tip 104 is formed with a transverse throughgoing bore 161 transverse to the longitudinal syringe assembly centerline 101. The distal syringe tip 104 includes a lumen 162 co-axial with the longitudinal syringe assembly centerline 101 and in flow communication with a proximal side of the transverse throughgoing bore 161. The distal syringe tip 104 includes a liquid drug dispensing lumen 163 co-axial with the longitudinal syringe assembly centerline 101 and in flow communication with a distal side of the transverse throughgoing bore 161. The liquid drug dispensing lumen 163 is fitted with an intradermal needle 121.

The syringe 102 includes a generally tubular flow control member 164 with a sealed end 166. The flow control member 164 includes a peripheral flow control member surface 167 having a transverse flat cutout 168 and a peripheral groove 169. The flat cutout 168 has a first cutout end 171 and a second cutout end 172. The peripheral groove 169 is in flow communication with the second cutout end 172.

The drug vial adapter 106 includes an internal semi-circular cam surface 173 contacting the sealed end 166. The cam surface 173 has a start cam surface end 174 and a final cam surface end 176. The start cam surface end 174 has a separation S1 from the longitudinal syringe assembly centerline 101. The final cam surface end 176 has a separation S2 from the longitudinal syringe assembly centerline 101. The separation S1 is greater than the separation S2 such that rotation of the drug vial adapter 106 urges the flow control member 164 from an initial flow path position to a final flow path position.

Figure 10:
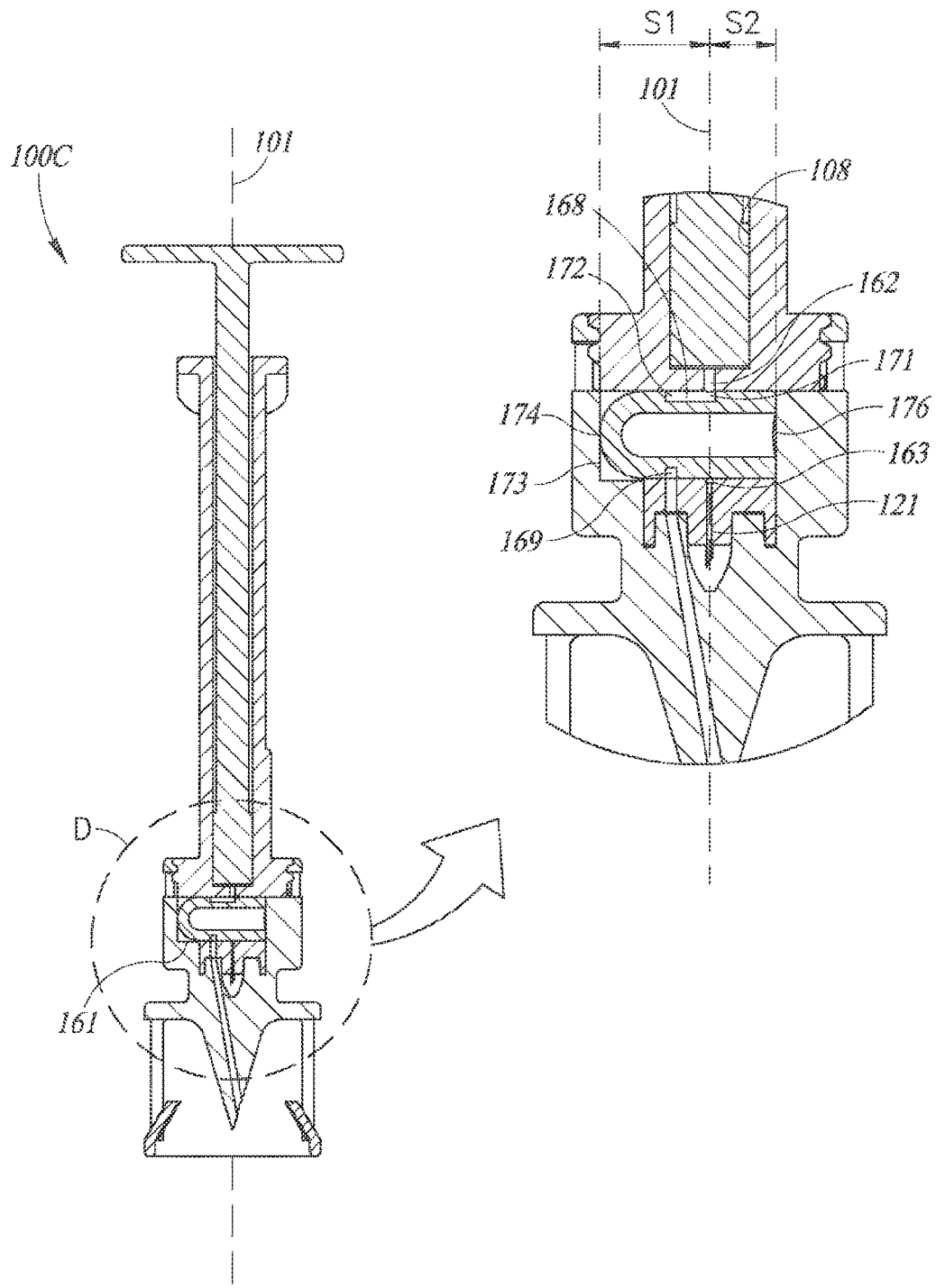
FIG. 10 is a longitudinal cross section of the FIG. 8 syringe assembly with its flow control member in an initial flow path position and an enlargement of encircled region D.

FIG. 10 shows the syringe assembly 100C in its initial flow path position with the start cam surface end 174 contacting the sealed end 166. FIG. 10 shows the syringe assembly 100C has an initial flow path between the syringe barrel interior 108 and the puncturing cannula 147 via the lumen 162, the flat cutout 168 at its first cutout end 171, the peripheral groove 169 and the liquid drug dispensing lumen 163.

Figure 11:
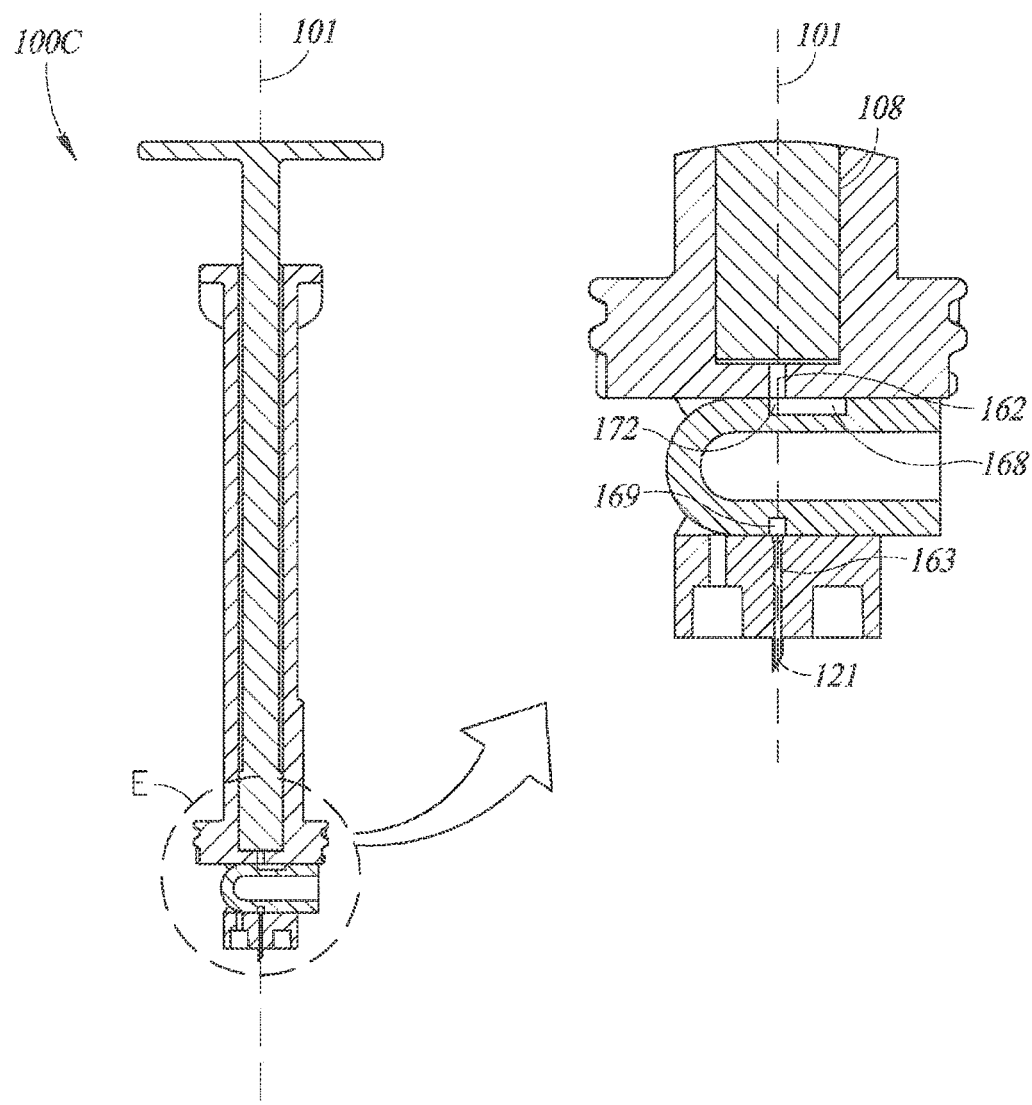
FIG. 11 is a longitudinal cross section of the FIG. 8 syringe assembly with its flow control member in a final flow path position and an enlargement of encircled region E.

FIG. 11 shows the syringe assembly 100C in its final flow path position after detachment of the drug vial adapter 106 with the cam surface 166 having urged the flow control member 164 transversely across the longitudinal syringe assembly centerline 101. FIG. 11 shows the syringe assembly 100C has a final flow path between the syringe barrel interior 108 and the intradermal needle 121 via the lumen 162, the flat cutout 168 at its second cutout end 172, the peripheral groove 169 and the liquid drug dispensing lumen 163.

Figure 12:
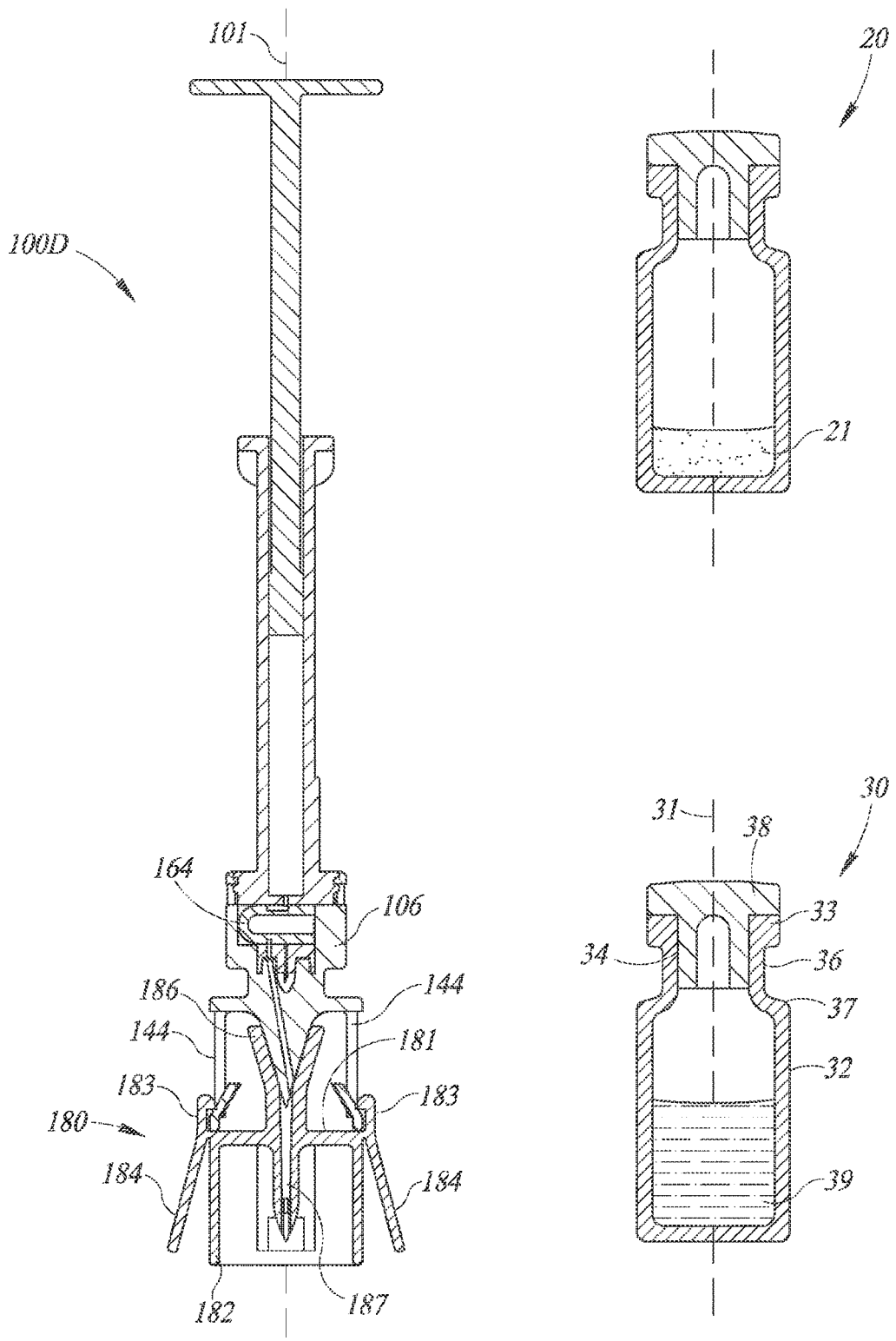
FIG. 12 is a longitudinal cross section of the FIG. 8 syringe assembly modified for use with a drug vial containing powder medicament and a liquid vial containing liquid contents.

FIG. 12 shows a syringe assembly 100D for use with a drug vial 20 and a liquid vial 30. The drug vial 20 differs from the drug vial 10 insofar as it includes a powder medicament 21. The liquid vial 30 has a longitudinal liquid vial centerline 31 and includes a liquid vial tube 32, a tubular liquid vial crown 33 having a liquid vial crown opening 34 and a narrow diameter liquid vial neck 36 intermediate the liquid vial tube 32 and the liquid vial crown 33. The liquid vial 30 includes a liquid vial shoulder 37 intermediate the liquid vial tube 32 and the liquid vial neck 36. The liquid vial 30 includes a liquid vial stopper 38 for stopping the liquid vial crown opening 34. The liquid vial 30 contains liquid contents 39 for mixing with the powder medicament 21 to form liquid drug contents 19. The liquid contents 39 can be either diluent for reconstitution purposes only or include an active component.

The syringe assembly 100D additionally includes a liquid vial adapter 180 for telescopic mounting on the liquid vial 30. The liquid vial adapter 180 has a transverse liquid vial adapter top wall 181 formed with a downward depending skirt 182 for telescopic mounting on the liquid vial 30. The liquid vial adapter 180 is formed with a diametric pair of clips 183 for clipping inside the diametric pair of longitudinal directed apertures 144 for mounting the liquid vial adapter 180 on the drug vial adapter 106. The clips 183 have downward depending finger operated release members 184 for releasing the liquid vial adapter 180 from the drug vial adapter 106 on applying a compression force thereon towards the longitudinal syringe assembly centerline 101. The liquid vial adapter top wall 181 is formed with an upright conical shaped port 186 for receiving the puncturing cannula 147. The liquid vial adapter top wall 181 is formed with a downward depending puncturing cannula 187 for puncturing the liquid vial 30 on telescopic mounting the liquid vial adapter 180 thereon. The port 186 is in continuous flow communication with the puncturing cannula 187 thereby affording flow communication between the syringe 102 and the puncturing cannula 187 in the initial flow path position of the flow control member 164.

Figure 13C:
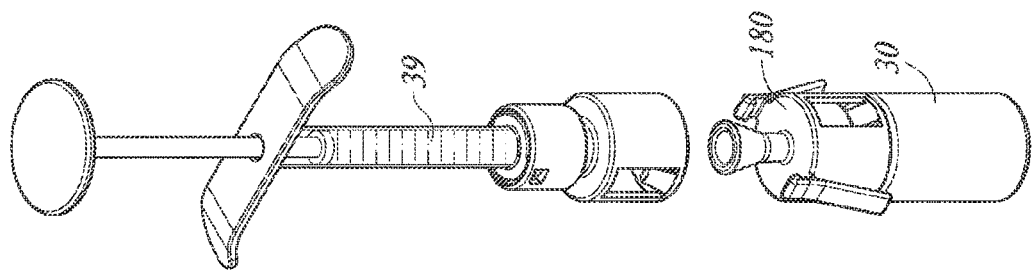
FIG. 13A to FIG. 13G show the use of the FIG. 12 syringe assembly for reconstituting and administering liquid drug contents.
Figure 13B:
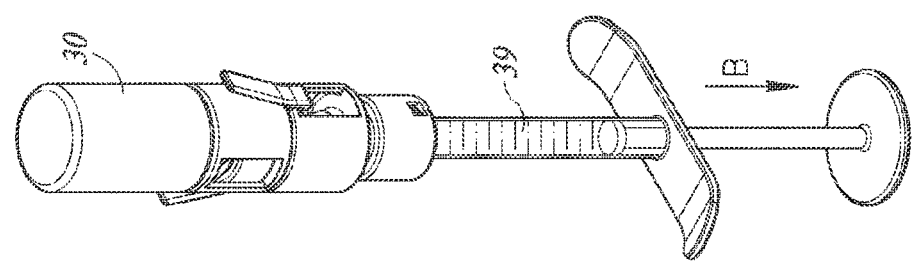
Figure 13A:
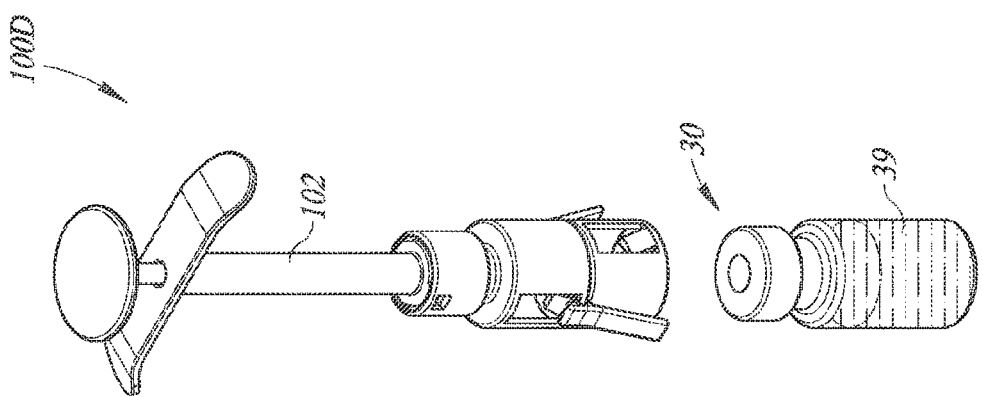
Figure 13G:
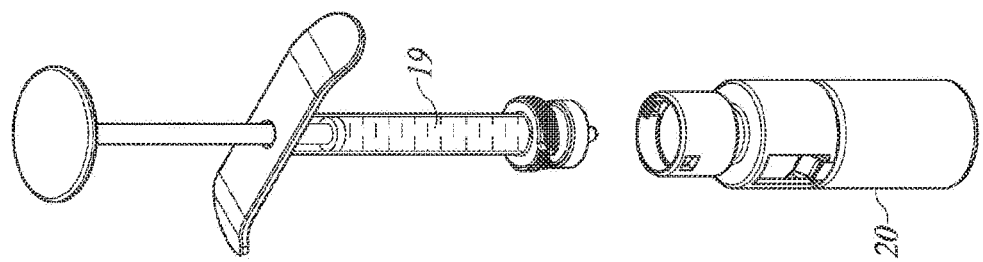
Figure 13F:
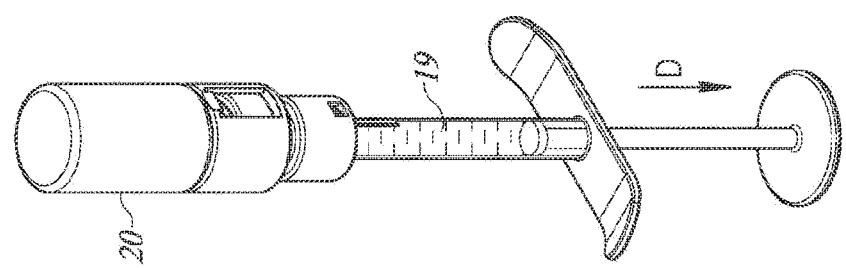
Figure 13E:
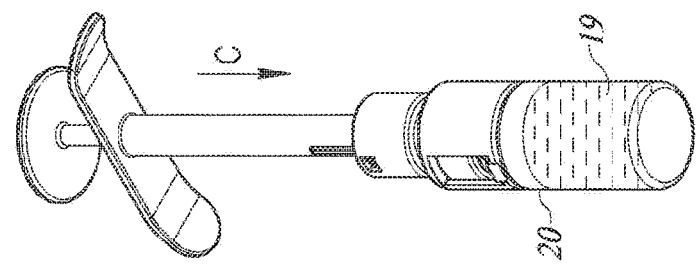
Figure 13D:
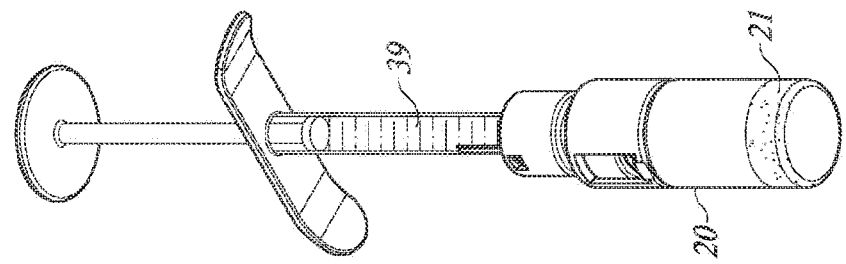

FIG. 13A to FIG. 13G show the use of the syringe assembly 100D for administering liquid drug contents 19. FIG. 13A shows the syringe assembly 100D in its initial flow path position and an empty syringe 102 with a fully inserted plunger 109. A clinical practitioner telescopic mounts the liquid vial adapter 180 on the liquid vial 30 for puncturing same. FIG. 13B shows the clinical practitioner inverts the syringe assembly 100D and the punctured liquid vial 30 to aspirate the liquid contents 39 from the liquid vial 30 into the syringe 102 as denoted by arrow B. FIG. 13C shows the clinical practitioner inverts the syringe assembly 100D and detaches the liquid vial adapter 180 and the now empty liquid vial 30. FIG. 13D shows the clinical practitioner telescopically mounts the syringe assembly 100D with the liquid contents 39 on the drug vial 20 for puncturing same. FIG. 13E shows the clinical practitioner injects the liquid contents 39 into the drug vial 20 as denoted by arrow C to reconstitute the powder medicament 21 to liquid drug contents 19. FIG. 13F shows the clinical practitioner inverts the syringe assembly 100D and the punctured drug vial 20 to aspirate the liquid drug contents 19 from the drug vial 20 into the syringe 102 as denoted by arrow D. FIG. 13G shows the clinical practitioner inverts the syringe assembly 100D and the now empty drug vial 20 to its upright position. The clinical practitioner rotates the drug vial adapter 106 through a half turn to detach it together with the empty drug vial 20 from the distal syringe tip 104 to expose the intradermal needle 121 and urge the flow control member 164 to its final flow path position. The syringe 102 is ready for administering the liquid drug contents 19.

While the invention has been described with respect to a limited number of embodiments, it will be appreciated that many variations, modifications, and other applications of the invention can be made within the scope of the appended claims.

The invention claimed is:

1. A syringe assembly for use with a drug vial having a close ended drug vial tube, a tubular drug vial crown having a drug vial crown opening and a drug vial stopper for stopping the drug vial crown opening, the drug vial containing liquid drug contents, the syringe assembly having a longitudinal syringe assembly centerline and comprising:

(a) a syringe including a proximal syringe end and a distal syringe tip, said syringe including an open ended syringe barrel having a proximal syringe barrel end and a distal syringe barrel end;

(b) a liquid drug administration device for administrating the liquid drug contents; and (c) a puncturing cannula for puncturing the drug vial stopper, said puncturing cannula being in flow communication with said syringe barrel;

wherein the liquid drug administration device is integral with the distal syringe tip, and the syringe assembly further comprises:

(d) a unitary drug vial adapter including a proximal tubular stem manually detachably mounted on said distal syringe tip, a distal downward depending skirt for telescopic mounting on the drug vial, an intermediate neck between said proximal tubular stem and said distal downward depending skirt, and said puncturing cannula for puncturing the drug vial stopper on said telescopic mounting said drug vial adapter on the drug vial, said puncturing cannula includes a lumen extending between an aperture in a portion of the intermediate neck and an aperture at a puncturing cannula tip, and (e) a flow control member displaceable from an initial flow path position to a final flow path position, said flow control member having an underside configured to mate with said portion of said intermediate neck and arranged to provide a flow path between said puncturing cannula and said syringe barrel in said initial flow path position of said flow control member in an initial set-up position of the syringe assembly in which said drug vial adapter is initially detachably mounted on said distal syringe tip, the syringe assembly being such that, on manual detachment of said drug vial adapter from said distal syringe tip, including a manual rotation of said drug vial adapter relative to said syringe, the manual rotation of said drug vial adapter displaces said flow control member from said initial flow path position to said final flow path position, said flow control member arranged to provide a flow path between said syringe barrel and said liquid drug administration device in said final flow path position for enabling administering the liquid drug contents.

2. The assembly according to claim 1 wherein said manual detachment includes a manual rotation of said drug vial adapter relative to said syringe about the longitudinal syringe assembly centerline.

3. The assembly according to claim 2 wherein said flow control member is rotatable about the longitudinal syringe assembly centerline and includes an initial flow path lumen for flow communication between said syringe barrel and said puncturing cannula in said initial flow path position and a final flow path lumen for flow communication between said syringe barrel and said integral liquid drug administration device in said final flow path position and said manual rotation of said drug vial adapter concurrently rotates said flow control member from said initial flow path position to said final flow path position during detachment of said drug vial adapter from said distal syringe tip.

4. The assembly according to claim 2 wherein said flow control member is transversely displaceable with respect to the longitudinal syringe assembly centerline from an initial flow path position for flow communication between said syringe barrel and said puncturing cannula to a final flow path position for flow communication between said syringe barrel and said integral liquid drug administration device and said drug vial adapter includes an internal cam surface for transversely displacing said flow control member from said initial flow path position to said final flow path position during said manual rotation of said drug vial adapter for detachment from said distal syringe tip.

5. A syringe assembly for use with a drug vial and a liquid vial, the drug vial having a close ended drug vial tube containing drug contents, a tubular drug vial crown having a drug vial crown opening, and a drug vial stopper for stopping the drug vial crown opening, the liquid vial including a liquid vial tube, a tubular liquid vial crown with a liquid vial crown opening and a liquid vial stopper for stopping the liquid vial crown opening, the liquid vial containing liquid contents for forming the liquid drug contents in the drug vial, the syringe assembly having a longitudinal syringe assembly centerline and comprising:

(a) a syringe including a proximal syringe end and a distal syringe tip, said syringe including an open ended syringe barrel having a proximal syringe barrel end and a distal syringe barrel end;

(b) a liquid drug administration device for administrating the liquid drug contents; and (c) a puncturing cannula for puncturing the drug vial stopper, said puncturing cannula being in flow communication with said syringe barrel;

wherein the liquid drug administration device is integral with the distal syringe tip, and the syringe assembly further comprises:

(d) a drug vial adapter including a proximal tubular stem manually detachably mounted on said distal syringe tip, a distal downward depending skirt for telescopic mounting on the drug vial, and said puncturing cannula for puncturing the drug vial stopper on said telescopic mounting said drug vial adapter on the drug vial, and (e) a flow control member displaceable from an initial flow path position to a final flow path position, said flow control member arranged to provide a flow path between said puncturing cannula and said syringe barrel in said initial flow path position of said flow control member in an initial set-up position of the syringe assembly in which said drug vial adapter is initially detachably mounted on said distal syringe tip, the syringe assembly being such that, on manual detachment of said drug vial adapter from said distal syringe tip, including a manual rotation of said drug vial adapter relative to said syringe, the manual rotation of said drug vial adapter displaces said flow control member from said initial flow path position to said final flow path position, said flow control member arranged to provide a flow path between said syringe barrel and said liquid drug administration device in said final flow path position for enabling administering the liquid drug contents, the assembly further comprising a liquid vial adapter including a detachable mounting arrangement for manually detachably mounting said liquid vial adapter downward depending from said drug vial adapter, a downward depending skirt for telescopic mounting on the liquid vial, a puncturing cannula for puncturing the liquid vial stopper on said telescopic mounting said liquid vial adapter on the liquid vial and a conical shaped port for receiving said drug vial adapter's puncturing cannula on said mounting said liquid vial adapter on said drug vial adapter.

* * * * *